US008175815B2

(12) United States Patent
Avdeef et al.

(10) Patent No.: US 8,175,815 B2
(45) Date of Patent: May 8, 2012

(54) METHOD FOR ASSESSING ABSORPTION PROPERTIES OF LOW SOLUBILITY COMPOUNDS

(75) Inventors: Alex Avdeef, Sommerville, MA (US); Manfred Kansy, Freiburg (DE)

(73) Assignees: F. Hoffmann-La Roche AG, Basel (CH); pION Inc., Woburn, MA (US)

( * ) Notice: Subject to any disclaimer, the term of this patent is extended or adjusted under 35 U.S.C. 154(b) by 830 days.

(21) Appl. No.: 12/224,449

(22) PCT Filed: Feb. 27, 2007

(86) PCT No.: PCT/CH2007/000097
§ 371 (c)(1),
(2), (4) Date: Aug. 26, 2008

(87) PCT Pub. No.: WO2007/098625
PCT Pub. Date: Sep. 7, 2007

(65) Prior Publication Data
US 2009/0187365 A1  Jul. 23, 2009

Related U.S. Application Data

(60) Provisional application No. 60/777,976, filed on Feb. 28, 2006.

(51) Int. Cl.
*G01N 31/00* (2006.01)
*C08B 11/20* (2006.01)
(52) U.S. Cl. ............... 702/22; 702/23; 702/30; 536/87
(58) Field of Classification Search ........................ None
See application file for complete search history.

(56) References Cited

U.S. PATENT DOCUMENTS 6,569,686 B2 * 5/2003 Avdeef et al. ................ 436/166
7,022,528 B2 * 4/2006 Avdeef et al. ................ 436/172

FOREIGN PATENT DOCUMENTS

| WO | WO 03/065037 A2 * | 8/2003 |
| WO | WO 2005/095950 | 10/2005 |
| WO | WO 2005/118141 A2 * | 12/2005 |

OTHER PUBLICATIONS

Amidon, G.L. et al., A theoretical basis for a biopharmaceutic drug classification: the correlation of in vitro drug product dissolution and in vivo bioavailability. Pharm. Res. 1995, 12, 413-420.
Avdeef, A. High-throughput measurement of permeability profiles. In: van de Waterbeemd, H.; Lennernäs, H.; Artursson, P.(Eds.). Drug Bioavailability. Estimation of Solubility, Permeability, Absorption and Bioavailability. Wiley—VCH: Weinheim, 2002, pp. 46-71.
Avdeef, A. High-throughput measurements of solubility profiles. In: Testa, B., van de Waterbeemd, H., Folkers, G., Guy, R. (Eds.), Pharmacokinetic Optimization in Drug Research, Verlag Helvetica Chimica Acta: Zürich and Wiley—VCH: Weinheim, 2001, pp. 305-326.

Avdeef, A. pH-metric solubility. 1. Solubility-pH profiles from Bjerrum plots. Gibbs buffer and $pK_a$ in the solid state. *Pharm. Pharmacol. Commun.* 1998, 4, 165-178.
Avdeef, A. *Absorption and Drug Development: Solubility, Permeability and Charge State.* Wiley & Sons Wiley-Interscience, 2003, pp. 116-246.
Avdeef, A. *Absorption and Drug Development: Solubility, Permeability and Charge State.* Wiley & Sons, 2003, pp. 7-21.
Avdeef, A. High-Throughput Solubility, Permeability, and the MAD PAMPA Model. In: Testa, B.; Krämer, S.D.; Wunderli-Allenspach, H.; Folkers, G. (Eds.), Pharmacokinetic Profiling in Drug Research. Wiley-VCH: Zürich 2006, pp. 221-241.
Avdeef, A. Physicochemical Profiling (Permeability, Solubility and Charge State). *Curr. Topics Med. Chem.* 2001, 1, 277-351.
Avdeef, A. The Rise of PAMPA. *Expert Opin. Drug Metab. Toxicol.* 2005, 1, 325-342.
Avdeef, A., Artursson, P., Neuhoff, S., Lazorova, L., Gråsjö, J., Tavelin, S. Caco-2 permeability of weakly basic drugs predicted with the Double-Sink PAMPA $pK_a^{flux}$ method. *Eur. J. Pharm. Sci.* 2005, 24, 333-349.
Avdeef, A., Nielsen, P., Tsinman, O. PAMPA—a drug absorption in vitro model. 11. Matching the in vivo unstirred water layer thickness by individual-well stirring in microtitre plates. *Eur. J. Pharm. Sci.* 2004, 22, 365-374.
Avdeef, A.; Bendels, S.; Tsinman, O.; Tsinman, K.; Kansy, M. Solubility-Excipient Classification Gradient Maps. *Pharm. Res.* 2007, 24, 530-545.
Avdeef, A. et al., PAMPA-Excipient Classification Gradient Maps. *Pharm. Res.* 2006, 23, 2525-2535.
Avdeef, A.; Berger, C.M. pH-metric solubility. 3. Dissolution titration template method for solubility determination. *Eur. J. Pharm. Sci.* 2001, 14, 281-291.
Avdeef, A. et al., pH-metric solubility. 2: Correlation between the acid-base titration and the saturation shake-flask solubility-pH methods. *Pharm. Res.* 2000, 17, 85-89.
Avdeef, A.; Bucher, J.J. Accurate measurements of the concentration of hydrogen ions with a glass electrode: calibrations using the Prideaux and other universal buffer solutions and a computer-controlled automatic titrator. *Anal. Chem.* 1978, 50, 2137-2142.

(Continued)

*Primary Examiner* — Lori A Clow
(74) *Attorney, Agent, or Firm* — Mintz Levin Cohn Ferris Glovsky and Popeo PC

(57) ABSTRACT

The invention deals with a method for the assessment of the effect of excipients, pH and combinations thereof on the predicted absorption properties of low solubility compounds, comprising the step of assessing a change in a flux function for a combination of a low solubility compound and an excipient at at least one predefined pH value. The method allows a fast, accurate, and economic evaluation of an excipient being capable of optimizing the absorption of drug molecules, i.e. low solubility compounds. Furthermore, animal experiments can be excluded and use of compounds can be reduced in such evaluation. Thus, screening for future formulation efficacy (pH and excipient effects on solubility and permeability) of drug candidates can be justified, since the method is fast, compound-sparing, cost-effective, and reasonably accurate.

20 Claims, 11 Drawing Sheets

OTHER PUBLICATIONS

Avdeef, A.; Comer, J.E.A.; Thomson, S.J. pH-metric log P. 3. Glass electrode calibration in methanol-water, applied to $pK_a$ determination of water-insoluble substances. Anal. Chem. 1993, 65, 42-49.

Avdeef, A.; Kearney, D.L.; Brown, J.A.; Chemotti, A.R. Jr. Bjerrum plots for the determination of systematic concentration errors in titration data. Anal. Chem.1982, 54, 2322-2326.

Avdeef, A.; Testa, B. Physicochemical profiling in drug research: a brief survey of the state-of-the-art of experimental techniques. *Cell. Molec. Life Sci.* 2002, 59,1681-1689.

Avdeef, A.; Voloboy, D.; Foreman, A. Dissolution—Solubility: pH, Buffer, Salt, Dual-Solid, and Aggregation Effects. In: Testa, B.; van de Waterbeemd, H. (Eds.). Comprehensive Medicinal Chemistry II, vol. 5 ADME-TOX Approaches. Elsevier: Oxford, UK, 2006, in press.

Bakatselou, V.; Oppenheim, R.C.; Dressman, J.B. Solubilization and wetting effects of bile salts on the dissolution of steroids. *Pharm. Res.* 1991, 8, 1461-1469.

Bergström, C.A.S.; Luthman, K.; Artursson, P. Accuracy of calculated pH-dependent aqueous drug solubility. *Eur. J. Pharm. Sci.* 2004, 22, 387-398.

Bermejo M., et al., PAMPA—a drug absorption in vitro model. 7. Comparing rat in situ, Caco-2, and PAMPA permeability of fluoroquinolones. *Eur. J. Pharm. Sci.* 2004, 21, 429-441.

Bouligand, Y.; Boury, F.; Devoisselle, J.-M.; Fortune, R.; Gautier, J.-C.; Girard, D.; Maillol, H.; Proust, J.-E. Ligand crystals and colloids in water-amiodarone systems. *Langmuir* 1998, 14, 542-546.

Chen, H. et al., A high-throughput combinatorial approach for the discovery of a Cremophor EL-free paclitaxel formulation. *Pharm. Res.* 2003, 20, 1302-1308.

Curatolo, W. Physical chemical properties of oral drug candidates in the discovery and exploratory development settings. Pharm. Sci. Tech. Today 1998, 1, 387-393.

Dressman, J.B. Dissolution testing of immediate-release products and its application to forecasting in vivo performance. In: Dressman, J.B.; Lennernäs, H. (eds.), Oral Drug Absorption, Marcel Dekker, Inc., New York, 2000, pp. 155-181.

Faller, B.; Wohnsland, F. Physicochemical parameters as tools in drug discovery and lead optimization.In: *Pharmacokinetic Optimization in Drug Research*. Testa B, van de Waterbeemd H, Folkers G, Guy R (Eds.), Verlag Helvetica Chimica Acta, Zürich and Wiley—VCH, Weinheim (2001): 257-274.

Fini, A.; Fazio, G.; Feroci, G. Solubility and solubilization properties of non-steroidal anti-inflammatory drugs. *Int. J. Pharm.* 1995, 126, 95-102.

Garcia, J.J.; Bolas, F.; Torrado, J.J. Bioavailability and efficacy characteristics of two different oral liquid formulations of albendazole. Int. J. Pharm. 2003, 250, 351-358.

Ginski, M.J. et al., Prediction of Dissolution-Absorption Relationships from a Continuous Dissolution/Caco-2 System, *AAPS Pharmsci.* 1999, 1(3), 1-12.

Glomme, A.; März, J.; Dressman, J.B. Comparison of a miniaturized shake-flask solubility method with automated potentiometric acid/base titrations and calculated solubilities. *J. Pharm. Sci.* 2005, 94, 1-16.

Guidance for Industry, Waiver of In Vivo Bioavailability and Bioequivalence Studies for Immediate-Release Solid Oral Dosage Forms Based on a Biopharmaceutics Classification System, FDA, Washingthon, D.C., USA Aug. 2000.

Higuchi, T.; Shih, F.-M.; Kimura, T.; Rytting, J.H. Solubility determination of barely aqueous-soluble organic solids. *J. Pharm. Sci.* 1979, 68, 1267-1272.

Ho, N.F.H.; Raub, T.J.; Burton, P.S.; Barsuhn, C.L.; Adson, A.; Audus, K.L., Borchardt, R., 2000. Quantitative approaches to delineate passive transport mechanisms in cell culture monolayers. In: Amidon, G.L., Lee, P.I., Topp, E.M. (Eds.). Transport Processes in Pharmaceutical Systems. Marcel Dekker: New York, N.Y., pp. 219-316.

Int'l Search Report for PCT/CH2007/000097, mailed Jun. 12, 2007, 3 pgs.

Jinno, J.; Oh, D.-M.; Crison, J.R.; Amidon, G.L. Dissolution of ionizable water-insoluble drugs: the combined effect of pH and surfactant. *J. Pharm. Sci.* 2000, 89, 268-274.

Johnson, K.; Swindell, A. Guidance in the setting of drug particle size specifications to minimize variability in absorption. Pharm. Res. 1996, 13, 1795-1798.

Kansy, M., Senner, F., Gubernator, K. Physicochemical high throughput screening: parallel artificial membrane permeation assay in the description of passive absorption processes. *J. Med. Chem.* 1998, 41, 1007-1010.

Kansy, M.; Avdeef, A.; Fischer, H. Advances in screening for membrane permeability: high-resolution PAMPA for medicinal chemists. *Drug Disc. Today: Technologies* 2004, 1, 349-355.

Kibbe, A.H. (ed.) Handbook of Pharmaceutical Excipients, 5$^{th}$ Ed., 2005.

Lipinski, C. Poor aqueous solubility—an industry wide problem in drug discovery. *Amer. Pharm. Rev.* 2002, 5, 82-85.

Lipinski, C.A. Drug-like properties and the causes of poor solubility and poor permeability. *J. Phamacol. Tox. Methods*. 2000, 44, 235-249.

Liu, H. et al., In vitro permeability of poorly aqueous soluble compounds using different solubilizers in the PAMPA assay with liquid chromatography/mass spectrometry detection. *Pharm. Res.* 2003, 20, 1820-1826.

Meylan, W.M.; Howard, P.H. Estimating log P with atom/fragments and water solubility with log P. *Perspect. Drug Discov. Des.* 2000, 19, 67-84.

Nielsen, P.E., Avdeef, A. PAMPA—a drug absorption in vitro model. 8. Apparent filter porosity and the unstirred water layer. *Eur. J. Pharm. Sci.* 2004, 22, 33-41.

Okimoto, K.; Rajewski, R.A.; Uekama, K.; Jona, J.A.; Stella, V.J. The interaction of charged and uncharged drugs with neutral (HP-β-CD) and anionically charged (SBE7-β- CD) β-cyclodextrins. *Pharm. Res.* 1996, 13, 256-264.

Rege, D.B., et al., Effect of Common Excipients on Caco-2 Transport of Low-Permeability Drugs, *J. Pharm. Sci.* 2001, 90(11), 1776-1786.

Roseman,T.J.; Yalkowsky, S.H. Physicochemical properties of prostaglandin $F_{2\alpha}$(tromethamine salt): solubility behavior, surface properties, and ionization constants *J. Pharm. Sci.* 1973, 62, 1680-1685.

Ruell, J.A.; Tsinman, O.; Avdeef, A. Acid-base cosolvent method for determining aqueous permeability of amiodarone, itraconazole, tamoxifen, terfenadine and other very insoluble molecules. Chem. Pharm. Bull (2004) 52: 561-565.

Ruell, J.A.; Tsinman, K.L.; Avdeef, A. PAMPA—a drug absorption in vitro model. 5. Unstirred water layer in iso-pH mapping assays and $pK_a^{flux}$-optimized design (pOD-PAMPA). *Eur. J. Pharm. Sci.* 2003, 20, 393-402.

Rytting, E.; Lentz, K.A.; Chen, X.-Q.; Qian, F.; Venkatesh, S. Aqueous and cosolvent solubility data for drug-like organic compounds. *The AAPS J.* 2005, 7, E78-E105 (www.aapsj.org).

Savolainen, J.; Järvinen, K.; Taipale, H.; Jarho P.; Loftsson, T.; Järvinen, T. Co-administration of a water-soluble polymer increases the usefulness of cyclodextrins in solid oral dosage forms. Pharm. Res. 1998, 15, 1696-1701.

Schanker, L.S. et al., Absorption of drugs from the rat small intestine. J. Pcol. Exp. Therap. 1958, 123, 81-88.

Shore, P.A.; Brodie, B.B.; Hogben, C.A.M. The gastric secretion of drugs: A pH Partition Hypothesis. J. Pcol. Exp. Therap. 1957, 119, 361-369.

Smith, S.W.; Anderson, B.D. Salt and mesophase formation in aqueous suspensions of lauric acid. *Pharm. Res.* 1993, 10, 1533-1543.

Streng, W.H.; Yu, D.H.-S.; Zhu, C. Determination of solution aggregation using solubility, conductivity, calorimetry, and pH measurements. *Int. J. Pharm.* 1996, 135, 43-52.

Taylor, P. Optimizing assays for automated platforms. *Modern Drug Discov.* 2002, December issue, 37-39.

Tye, H. Application of statistical 'design of experiments' methods in drug discovery. *Drug Discov. Today* 2004, 9, 485-491.

Uch, A.S.; Hesse, U.; Dressman, J.B. Use of 1-methyl-pyrrolidone as a solubilizing agent for determining the uptake of poorly soluble drugs. *Pharm. Res.* 1999, 16, 968-971.

van de Waterbeemd, H.; Smith, D.A.; Beaumont, K.; Walker, D.K. Property-based design: optimization of drug absorption and pharmacokinetics. J. Med. Chem. 2001, 44, 1313-1333.

van de Waterbeemd, H.; Smith, D.A.; Jones, B.C. Lipophilicity in PK design: methyl, ethyl, futile. *J. Comp.-Aided Molec. Des.* 2001, 15, 273-286.

Weiss, T.F. Cellular Biophysics. vol. I: Transport. The MIT Press: Cambridge, MA, 1996, Table of Contents.

Wells, J.I. Pharmaceutical Preformulation: The Physicochemical Properties of Drug Substances. Ellis Horwood Ltd.: Chichester, 1988.

Wen, X.; Liu, Z.; Zhu, T.; Zhu, M.; Jiang, K.; Huang, Q. Evidence for the 2:1 molecular recognition and inclusion behavior between β- and γ-cyclodextrins and cinchonine. *Bioorg. Chem.* 2004, 32, 223-233.

Zhu, C.; Streng, W.H. Investigation of drug self-association in aqueous solution using calorimetry, conductivity, and osmometry. *Int. J. Pharm.* 1996, 130, 159-168.

* cited by examiner

METHOD FOR ASSESSING ABSORPTION PROPERTIES OF LOW SOLUBILITY COMPOUNDS

RELATED APPLICATIONS

The subject application claims benefit to PCT application no. PCT/CH2007/000097, filed 27 Feb. 2007, and U.S. provisional patent application No. 60/777,976 filed 28 Feb. 2006, each disclosure of which is herein incorporated by reference.

TECHNICAL FIELD

The present invention relates to a method for the assessment of the effect of excipients, pH and combinations thereof on the predicted absorption properties of low solubility compounds according to the preamble of independent claim 1 and more particularly to a computer program being arranged for performing said method according to independent claim 20.

BACKGROUND ART

Human intestinal absorption (HIA) of ionizable compounds can depend simultaneously on three key properties: solubility, permeability, and pKa (Avdeef A., "Absorption and Drug Development", Wiley Interscience, NY, 2003). This association is exemplified by the Absorption Potential (Dressman J B et al., "J. Pharm. Sci.", 1985, 74, 588), the Biopharmaceutics Classification System (Guidance for Industry, "Waiver of In Vivo Bioavailability and Bioequivalence Studies for Immediate Release Solid Oral Dosage Forms Based on a Biopharmaceutics Classification System", FDA, Washington, D.C., USA, August 2000), and the Maximum Absorbable Dose function (Curatolo W. "Pharm. Sci. Tech. Today", 1998, 1, 387). In the simplest terms, Fick's laws of diffusion underlie all of these models.

In the intestine, water-soluble weak bases are better absorbed from slightly alkaline regions (e.g., in the distal ileum), and weak acids are better absorbed from slightly acidic regions (e.g., proximal jejunum). This was rationalized by Brodie and coworkers (Shore P A et al., "J. Pcol. Exp. Therap.", 1957, 119, 361), who introduced the pH Partition Hypothesis to explain the influence of pH on the intestinal absorption of ionizable drugs. Rat intestines were perfused in situ with a drug solution of varied pH. At the same time, the drug was injected intravenously. The concentration of the drug in the luminal perfusate was adjusted until there was no net transport across the intestinal wall, so that it was possible to define the blood-lumen barrier ratio $$D = \frac{[drug]_{BLOOD}}{[drug]_{LUMEN}} \quad (1)$$

If only the neutral form of the drug permeates, then equation (1) can be predicted from the pKa of the drug and the pH gradient between the two sides of the intestinal barrier (Shore P A et al., "J. Pcol. Exp. Therap." 1957, 119, 361):

$$D = \frac{(1 + 10^{-pK_a + pH_{BLOOD}})}{(1 + 10^{-pK_a + pH_{LUMEN}})} \quad (2)$$

Equation (2) is derived from the pH dependence of permeability, based on the well known Henderson-Hasselbalch (HH) equation. Direct measurement of in situ intestinal perfusion absorption rates confirmed the pH dependence, further supporting that theory and observation were well matched in these early experiments.

The pH Partition Hypothesis suggests that membrane permeability will be highest at the pH where the molecule is least charged. But this is also the pH where the molecule is least soluble. It is particularly important to note that in Brodie's work, all of the compounds tested have relatively high water solubility. At the site of absorption, the amount of the uncharged species and the tendency of the neutral species to cross the phospholipid membrane barrier are both important predictors of absorption. The intrinsic permeability coefficient, $P_o$, characterizes the membrane transport of the uncharged species. The concentration of the uncharged species, $C_o$, depends on the dose, the solubility, the $pK_a$ of a molecule, and the pH at the site of absorption, according to the HH equation.

Combinatorial chemistry programs have tended to select for higher molecular weight molecules, which are predictably low in solubility. 'Early warning' tools, such as Lipinski's 'Rule of 5' (Lipinski C., "Amer. Pharm. Rev." 2002, 5, 82), and computer programs that predict solubility from 2-D structure, attempt to weed out such molecules early in discovery programs. Still, many solubility-problematic molecules remain unrecognized, due to the overly simplistic early methods used to measure solubility, and the masking effect of organic solvents (e.g., dimethyl sulfoxide) used in discovery measurements. Arguably, nephelometry-based kinetic solubility measurements, although fast, are no more reliable than in silico prediction methods (Glomme A. et al. "J. Pharm. Sci.", 2005, 94, 1).

Measurement of solubility of sparingly soluble molecules, e.g. compounds or drugs, is challenging for a number of reasons. Notably, the HH equation only poorly predicts the pH dependence of sparingly soluble molecules (Bergström CAS et al., "Eur. J. Pharm. Sci.", 2004, 22, 387 and U.S. Pat. No. 6,569,686 B2), largely due to the prevalence of aggregates and micelle-like structures in solution. Such aggregates have unusually high solubility (in pH solutions where charged species persist), with a sensitive temperature dependence.

Permeability measurement is also fraught with substantial uncertainty, since results depend particularly on how assay pH, the aqueous boundary layer (ABL), and incomplete mass balance are treated in such assays (both cellular and artificial membrane permeability assay) by different laboratories (Avdeef A. et al., "Eur. J. Pharm. Sci.", 2005, 24, 333).

Thus, more accurate (but still fast) solubility, and permeability methods in the candidate selection stage in pharmaceutical research and development would be particularly helpful in recognizing at a much earlier time truly problematic molecules (Bergström CAS et al., "Eur. J. Pharm. Sci.", 2004, 22, 387 and Glomme A. et al. "J. Pharm. Sci.", 2005, 94, 1).

Besides the described effects of pH, solubility, and permeability on absorption processes, particularly on HIA processes, the use of excipients can essentially affect absorption processes, particularly absorption processes of sparingly soluble molecules. Taking into consideration the complexity of the above mentioned effects, the evaluation of suitable excipients being capable of optimizing the absorption processes is a very difficult task. Today, such evaluation is performed by conducting animal experiments. Animal experiments usually are comparably time consuming, cause comparably large efforts and are ethically controversial.

Therefore, there is a need for an ethically passable method allowing a fast, compound sparing, cost effective, and reasonably accurate prediction of absorption properties of sparingly soluble molecules, i.e. low solubility compounds or drugs, taking into account the effect of excipients on said absorption.

DISCLOSURE OF INVENTION

According to the invention this need is settled by a method as it is defined by the features of independent claim 1, and by a computer program as it is defined by the features of independent claim 20. Preferred embodiments are subject of the dependent claims.

In particular, the invention deals with a method for the assessment of the effect of excipients, pH and combinations thereof on the predicted absorption properties of low solubility compounds, comprising the step of assessing a change in a flux function for a combination of a low solubility compound and an excipient at least one predefined pH value.

"Low solubility" as used hereinbelow is based on the definitions of solubility in the Biopharmaceutics Classification System adopted by the United States Food and Drug Administration as a bioavailability-bioequivalence regulatory guideline ("FDA guidance for industry waiver of in vivo bioavailability and bioequivalence studies for immediate release solid oral dosage forms containing certain active moieties/active ingredients based on a biopharmaceutics classification system", CDERGUID\2062dft.wpd Draft, January 1999). In particular, the solubility scale is defined in terms of the volume, e.g. in milliliter (mL), of water required to dissolve the highest dose strength at the lowest solubility in a pH range of 1 to 8, with 250 mL being the dividing line between high solubility and low solubility. Thus, low solubility refers to incomplete dissolution of the highest dose in 250 mL in the pH range of 1 to 8.

"Flux function" as used hereinbelow relates to chapter 2 of Avdeef A., "Absorption and Drug Development", Wiley Interscience, NY, 2003 defining that the flux function corresponds to particles or mass passing a barrier per area unit and time unit.

More precisely, the following is described in said chapter 2: Fick's first law applied to a membrane shows that passive diffusion of a solute is the product of the diffusivity and the concentration gradient of the solute inside the membrane. The membrane/water apparent partition coefficient relates the latter internal gradient to the external bulk-water concentration difference between the two solutions separated by the membrane. For an ionizable molecule to permeate by passive diffusion most efficiently, the molecule needs to be in its uncharged form at the membrane surface (pH Partition Hypothesis). The amount of the uncharged form present at a given pH, which directly contributes to the flux, depends on several important factors, such as pH, binding to indigenous carriers (proteins and bile acids), self-binding (aggregate or micelle formation), and solubility (a solid-state form of self-binding). Low solubility enters the transport consideration as a thermodynamic 'speed attenuator,' as a condition that lowers the opportunity for transport. In this way, permeability and solubility are the linked kinetic and thermodynamic parts of transport across a membrane.

Consider a vessel divided into two chambers, separated by a homogeneous lipid membrane. The left side is the donor compartment, where the sample molecules are first introduced; the right side is the acceptor compartment, which at the start has no sample molecules. Fick's first law applied to homogeneous membranes at steady state is a transport equation, $$J = D_m dC_m/dx = D_m [C_m^0 - C_m^h]/h \quad (3)$$

where J is the flux, in units of mol cm$^{-2}$ s$^{-1}$, where $C_m^0$ and $C_m^h$ are the concentrations, in mol cm$^{-3}$ units, of the uncharged form of the solute within the membrane at the two water-membrane boundaries, and where $D_m$ is the diffusivity of the solute within the membrane, in units of cm$^2$ s$^{-1}$. At steady state, the concentration gradient, $dC_m/dx$, within the membrane is linear. Steady state takes about 3 minutes to be established in a membrane of thickness 125 µm, assuming the solution is very well stirred.

The limitation of equation (3) is that measurement of concentrations of solute within different parts of the membrane is very inconvenient. However, since it can be estimated or possibly measured the distribution coefficients between bulk water and the membrane, log $K_d$ (the pH-dependent apparent partition coefficient), equation (3) can be converted into a more accessible form, $$J = D_m K_d (C_D - C_A)/h \quad (4)$$

where the substitution of $K_d$ allows us to use bulk water concentrations in the donor and acceptor compartments, $C_D$ and $C_A$, respectively. (With ionizable molecules, $C_A$ and $C_D$ refer to the concentrations of the solute summed over all forms of charge state.) These concentrations may be readily measured by standard techniques. Equation (4) is still not sufficiently convenient, since $D_m$ and $K_d$ need to be estimated. It is a common practice to lump these parameters and the thickness of the membrane into a composite parameter, called 'membrane permeability,' $P_m$, $$P_m = D_m K_d/h \quad (5)$$

The relevance of equation (4), which predicts how quickly molecules pass through simple membranes, to solubility comes in the concentration terms. Consider 'sink' conditions, where $C_A$ is essentially zero. Equation (4) reduces to the following flux equation $$J = P_m C_D \quad (6)$$

Flux depends on the product of effective permeability of the solute times the concentration of the solute summed over all charge state forms at the water-side of the donor surface of the membrane. This concentration ideally may be equal to the dose of the drug, unless the dose exceeds the solubility limit at the pH considered, in which case it is equal to the solubility. Since the uncharged molecular species is the permeant, equation (6) may be restated as $$J = P_o C_o <= P_o S_o \quad (7)$$

where $P_o$ and $C_o$ are the intrinsic permeability and concentration of the uncharged species, respectively. The intrinsic permeability does not depend on pH, but its cofactor in the flux equation, $C_o$, does. The concentration of the uncharged species is always equal to or less than the intrinsic solubility of the species, $S_o$, which also does not depend on pH.

Note that for the uncharged species, equation (5) takes on the form $$P_o = D_m K_p/h \quad (8)$$

where $K_p = C_m(0)/C_{Do}$; also, $K_p = C_m(h)/C_{Ao}$; $C_{Do}$ and $C_{Ao}$ are the aqueous solution concentrations of the uncharged species in the donor and acceptor sides, respectively.

In solutions saturated (i.e., excess solid present) at some pH, the plot of log $C_o$ versus pH for an ionizable molecule is extraordinary simple in form: it is a combination of straight segments, joined at points of discontinuity indicating the boundary between the saturated state and the state of complete dissolution. The pH of these junction points is dependent on the dose used in the calculation, and the maximum value of log $C_o$ is always equal to log $S_o$ in a saturated solution.

The method according to the invention allows a fast, accurate, and economic evaluation of an excipient being capable of optimizing the absorption of molecules, i.e. low solubility compounds or drugs. Furthermore, animal experiments can be excluded and use of compounds can be reduced in such evaluation. Thus, screening for future formulation efficacy (pH and excipient effects on solubility and permeability) of drug candidates can be justified, since the method is fast, compound-sparing, cost-effective, and reasonably accurate.

In a first preferred embodiment of the method according to the invention, assessing the change of the flux function comprises the steps of: preparing a calibration donor solution at a predefined pH value comprising the compound; preparing a donor solution at the predefined pH value comprising the compound and the excipient; preparing a receiver solution at the predefined pH value free of the compound and the excipient; providing the calibration donor solution into a first donor chamber being separated from a first receiver chamber by a barrier, providing the donor solution into a second donor chamber being separated from a second receiver chamber by the barrier and providing the receiver solution into the first and the second receiver chambers; incubating said solutions for a predefined period of time; and measuring the response of the compound in the receiver solution of the first and the second receiver chambers. The term "response" as used hereinbelow comprises dimensions suitable to assess the change of the flux function, particularly the concentration. Such a method allows for an efficient assessment of the effect of the excipient on the absorption properties of the compound. Further, it allows a highly automated processing, particularly when being performed in suitable devices such as for example in a device as it is described in U.S. Pat. No. 7,022,528 B2.

Preferably, assessing the change of the flux function comprises a repeated performing of the steps described above at a plurality of predefined pH values. Repeating in that context is not limited to chronologically processing the steps at one pH value after another but particularly also includes parallel processing of the steps at a plurality of pH values at the same time. Such an assessing allows to expand the effect on the absorption properties of the compound to pH related effects and to combine the effect of the excipient with the pH related effects. All said effects can then be taken into consideration for evaluation of an excipient, such that quality of evaluation can be improved without substantially impairing the efficiency of the evaluation. It can be advantageous to choose the plurality of pH values from the range of about pH 5 to about pH 7.5, particularly the plurality of pH values can comprise for example the values pH 5, pH 6.2, and pH 7.5.

Preferably, assessing the change of the flux function further comprises the step of determining a ratio between the measurement of the response, e.g. the concentration, of the compound in the receiver solution of the first receiver chamber and the measurement of the response, e.g. the concentration, of the compound in the receiver solution of the second receiver chamber. Such a ratio allows a convenient representation of the flux function such that a plurality of ratios based on a plurality of compounds, a plurality of excipients and a plurality of pH values can be conveniently displayed and overviewed.

Preferably, measuring the response, e.g. the concentration, of the compound in the receiver solution of the first and the second receiver chambers comprises the measurement of spectroscopic properties of the receiver solution. Such measurement of spectroscopic properties can be performed by various methods known in the art, such as for example by liquid chromatography-mass spectrometry, ultraviolet/visible absorption spectroscopy, infrared spectroscopy, emission spectroscopy, Raman spectroscopy, or the like. Using suitably devices performing such methods allows a fast and efficient measuring of the response, i.e. in particular the concentration, of the compound in the receiver solution.

Preferably, the barrier is selected from the group consisting of human tissues, animal tissues, plant tissues, cultured-cell models, and artificial membranes. Barrier in this context particularly relates to active or passive diffusion barriers mimicking physical and chemical properties of biological barriers. Thus, lipophilic barriers are further preferred.

Preferably, assessing the change of the flux function is performed for a plurality of compounds and a plurality of excipients by: preparing a plurality of donor solutions at the predefined pH value comprising each combination of each of the plurality of compounds and each of the plurality of excipients; providing the plurality of donor solutions into a plurality of second donor chambers being separated from a plurality of second receiver chambers by the barrier and providing the receiver solution into the plurality of second receiver chambers; and measuring the response, e.g. the concentration, of the compound in the receiver solution of the plurality of second receiver chambers. Such a parallel processing allows an efficient and fast assessing of the flux function for a plurality of compounds, a plurality of excipients and a plurality of pH values. Said parallel processing can for example be performed using the method and the device described in U.S. Pat. No. 7,022,528 B2.

In a second preferred embodiment of the method according to the invention, assessing the change of the flux function comprises the steps of: preparing a calibration donor solution at a predefined pH value comprising the compound; preparing a donor solution at the predefined pH value comprising the compound and the excipient; measuring the solubility of the compound in the calibration donor solution and in the donor solution; measuring the permeability of the calibration donor solution and of the donor solution; and combining the permeability measurement results and the solubility measurement results into the flux function. Such a method allows for an efficient assessment of the effect of the excipient on the absorption properties of the compound. Particularly, it combines changes in both permeability and solubility to monitor effect of excipients on the absorption potential of compounds without explicitly determining permeability and solubility as separate entities what makes the second embodiment of the method according to the invention particularly fast. It can comprise monitoring the change in response, e.g. in concentration, of the compounds appearing in a receiver chamber of a two chamber permeation system, the two chambers divided by a lipophilic barrier, while varying the excipient components (type and/or concentration) in a donor chamber. The barrier can constitute an artificial membrane (e.g., a filter impregnated with a lipophilic solution, i.e., the parallel artificial membrane permeability assay (PAMPA) model), cultured endothelial cells (e.g., RBE4), or other cultured cell models (e.g., Caco-2, MDCK, etc.). Consideration of the biologically relevant aqueous boundary layer thickness and pH can also be taken into account. This second embodiment of the method according to the invention leads to a high-throughput pre-formulation screening technique, which allows early, fast, and cost effective assessment of the influence of excipients on absorption and the pharmacokinetic properties of research compounds.

Preferably, assessing the change of the flux function comprises a repeated performing of the steps described above at a plurality of predefined pH values. With respect to the expression "repeating" the above mentioned also applies hereinbelow. Such an assessing allows to expand the effect on the absorption properties of the compound to pH related effects and to combine the effect of the excipient with the pH related effects. All said effects can then be taken into consideration for evaluation of an excipient, such that quality of evaluation can be improved without substantially impairing the efficiency of the evaluation. It can be advantageous to choose the plurality of pH values from the range of about pH 5 to about pH 7.5, particularly the plurality of pH values can comprise for example the values pH 5, pH 6.2, and pH 7.5.

Thereby, the measuring of the solubility of the compound in the calibration donor solution and in the donor solution preferably comprises the steps of: incubating said solutions for a predefined period of time; filtering said solutions; and measuring the amount of compound in the filtered solutions. Such measuring can be performed in an efficient, fast, and accurate manner by performing various processes known in the art, wherein it can be particularly advantageous to use the method and the device described in U.S. Pat. No. 7,022,528 B2.

Preferably, the measuring of the permeability of the calibration donor solution and of the donor solution comprises the steps of: preparing a receiver solution at the predefined pH value free of the compound and the excipient; providing the calibration donor solution into a first donor chamber being separated from a first receiver chamber by a membrane filter, providing the donor solution into a second donor chamber being separated from a second receiver chamber by the membrane filter and providing the receiver solution into the first and the second receiver chambers; incubating said solutions for a predefined period of time; and measuring the amount of compound in the donor solutions of the first and the second donor chambers and in the receiver solution of the first and the second receiver chambers. Again, such measuring can be performed in an efficient, fast, and accurate manner by performing various processes known in the art, wherein it can be particularly advantageous to use the method and the device described in U.S. Pat. No. 7,022,528 B2.

Preferably, assessing the change of the flux function further comprises the step of determining a ratio between the measurement of the amount of compound in the receiver solution of the first receiver chamber and the measurement of the amount of the compound in the receiver solution of the second receiver chamber. Such a ratio allows a simple representation of the flux function such that a plurality of ratios based on a plurality of compounds, a plurality of excipients and a plurality of pH values can be conveniently displayed and overviewed.

Preferably, assessing the change of the flux function is performed for a plurality of compounds and a plurality of excipients by: preparing a plurality of donor solutions at the predefined pH value of each combination of each of the plurality of compounds and each of the plurality of excipients; measuring the solubility of the compound in each of the donor solutions; and measuring the permeability of each of the donor solutions. Such a parallel processing allows an efficient and fast assessing of the flux function for a plurality of compounds, a plurality of excipients and a plurality of pH values. Said parallel processing can for example be performed using the method and the device described in U.S. Pat. No. 7,022,528 B2.

In all preferred embodiments of the method according to the invention described above the receiver solution preferably comprises at least one additive. Such an additive can effect the assessing of the change of the flux function to suitable conditions. For example, the conditions can be adapted to more closely represent in vivo intestinal environment by means of additives. Further, the conditions can for example be adapted to allow an improved or easier processing.

Preferably, the additive has at least one of the properties selected from the group of high binding-capacity for the compound, low absorption of ultraviolet light, high water solubility, and low vapour pressure.

Preferably, the method according to the invention comprises the step of stirring the calibration donor solution and the donor solution. By means of such stirring the conditions for assessing of the change of the flux function can be optimized. For example, it can be prevented that microconditions close to the barrier not representing the aimed environment are provided during assessing of the change of the flux function. This is for example of particular interest, if an intestinal environment is to be represented in which both sides of the natural barrier underlie a certain flow in vivo. Thus, such stirring can help to simulate the function of the blood as a sink and thereby the diffusion gradient around the barrier can be maintained.

In a preferred embodiment the method comprises the steps of: rank ordering the ratios by excipient, compound and pH value; and visualizing the rank ordered ratios. Such rank ordering and visualisation allows to efficiently overview and to efficiently rate a plurality of compounds combined with a plurality of excipients at a plurality of pH values.

Preferably, the rank ordering of the ratios comprises the steps of: calculating ratio sums for each excipient over all compounds and over all pH values; and rank ordering the ratio sums. Building such sums for all excipients and rank ordering said sums can allow an even more efficient overview and an even more efficient rating of a plurality of compounds combined with a plurality of excipients at a plurality of pH values.

Preferably, the method further comprises the steps of: calculating further ratio sums for each compound over all excipients and over all pH values; and rank ordering the further ratio sums. Building additionally such sums for all compounds and rank ordering said sums can allow an even more efficient overview and an even more efficient rating of a plurality of compounds combined with a plurality of excipients at a plurality of pH values.

Another aspect of the invention deals with a computer program being arranged for performing all of or parts of the steps of the method described above. Using such a computer program allows to automatize substantial parts of the method such that it can be performed efficiently, fast, and accurately. Particularly, if the results of assessing a change in the flux function are visualized a quick evaluation of suitable excipients, drugs, and pH values can be performed.

BRIEF DESCRIPTION OF DRAWINGS

The method according to the invention and the computer program according to the invention are described in more detail hereinbelow by way of exemplary embodiments and with reference to the attached drawings, wherein.

MODE(S) FOR CARRYING OUT THE INVENTION

Figure 1:
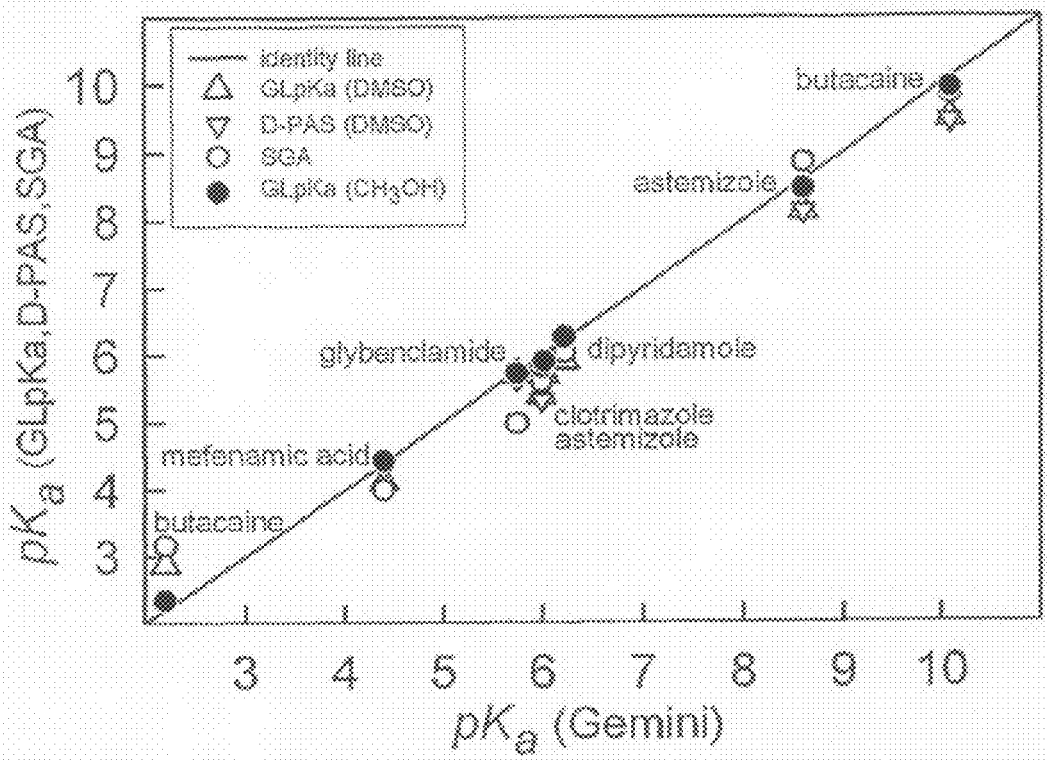
FIG. 1 shows comparisons of $pK_a$ determination methods for an example of permeability measurements of a first embodiment of the method according to the invention.

A first embodiment of the method according to the invention comprises combining permeability measurement results and solubility measurement results into a flux function for the assessment of the effect of excipients, pH and combinations thereof on the predicted absorption properties of low solubility compounds.

Appropriate permeability measurement can be performed in various manner. In discovery, cultured monolayer cell models, such as Caco-2 or Madin-Darby canine kidney (Ho N. F. H. et al., "Quantitative approaches to delineate passive transport mechanisms in cell culture monolayers", 2000 in: Amidon G. L. et al., "Transport Processes in Pharmaceutical Systems", Marcel Dekker, New York, pp. 219-316 and Avdeef A. et al., "Caco-2 permeability of weakly basic drugs predicted with the Double-Sink PAMPA pKa flux method", Eur. J. Pharm. Sci., 2005, 24, 333-349A), are often used. In pharmaceutical industry, by the time the selected candidate molecules are passed into the development phase, such cellular studies are not usually used to select excipients. Commonly, pharmacokinetic animal models are used at that stage. In the case of sparingly soluble, but otherwise promising molecules, early excipient screening, perhaps as a first step in early preclinical development, is beneficial in prioritizing and perhaps minimizing the number of animal measurements, if a cost effective means is available to measure the effect of excipients on permeability. Liu et al. (Liu, H. et al., "In vitro permeability of poorly aqueous soluble compounds using different solubilizers in the PAMPA assay with liquid chromatography/mass spectrometry detection", Pharm. Res., 2003, 20, 1820-1826) were the first to propose to do just that, using the low-cost parallel artificial membrane permeability assay (PAMPA) model specifically for screening the solubilizing agents Brij® 35, Cremophor EL, ethanol, and Tween 80. Up to that time, PAMPA had been a useful probe, but solely in early discovery screening. Since then, the value of PAMPA as a useful mechanistic tool for medicinal chemists has been demonstrated in several instances, but aside from the mentioned work of Liu et al., the impact of PAMPA in early preclinical development has not been substantiated.

In the permeability measurement described hereinbelow as a example for the first embodiment of the method according to the invention, it is proposed to extend the theme explored by Liu et al. The double sink PAMPA measurements of following eight sparingly soluble drugs are reported: astemizole, butacaine, clotrimazole, dipyridamole, griseofulvin, progesterone, glybenclamide, and mefenemic acid, measured under fifteen combinations of six excipients and ionic strength adjusters: sodium taurocholate, 2-hydroxypropyl-b-cyclodextrin, potassium chloride, propylene glycol, 1-methyl-2-pyrrolidone, and polyethylene glycol 400, to assess the effect of excipients on permeability.

The example of permeability measurement is performed using double sink PAMPA and a double sink PAMPA suitable lipid from the company pION (PN 1100669) as follows: The compounds used in this example of permeability measurement are the compounds listed in Table 1. The double sink PAMPA lipid is stored at −20° C. when not used. The pH of the assayed donor solutions is adjusted with universal buffers from the company pION (PN 100621, 1100151), and the buffer solution at pH 7.4 containing a chemical scavenger buffer from the company pION ASB-7.4 (PN 110139) to simulate serum proteins is used as the receiver solution. Excipients are added only to the donor wells.

TABLE 1

| COMPOUND | $pK_a$ 25° C., 0.15 M KCl | wt % $CH_3OH$ | slope | GOF | n |
|---|---|---|---|---|---|
| Astemizole | 5.99 ± 0.06 | 40-61 | −0.012 | 2.2 | 6 |
|  | 8.60 ± 0.04 | 40-61 | −0.013 | 1.6 | 6 |
| Butacaine | 2.20 ± 0.11 | 16-57 | −0.008 | 1.4 | 6 |
|  | 10.09 ± 0.10 | 16-57 | −0.021 | 5.4 | 6 |
| Clotrimazole | 6.02 ± 0.05 | 11-49 | −0.020 | 3.6 | 6 |
| Dipyridamole | 6.22 ± 0.15 | 5-43 | −0.016 | 3.3 | 6 |
| glybenclamide | 5.75 ± 0.15 | 35-75 | 0.008 | 3.0 | 7 |
| mefenamic acid | 4.39 ± 0.09 | 44-74 | 0.018 | 1.7 | 8 |

With respect to the excipients and its concentrations, quantities of six excipients are selected to overlap the concentrations expected in a gastrointestinal fluid under clinically relevant conditions. For KCl, two levels are selected: 0.1 Mole (M) and 0.2 M, according to their concentration in FASSIF/FESSIF media (Dressman J. B., "Dissolution testing of immediate-release products and its application to forecasting in vivo performance", in Dressman J. B. et al., "Oral Drug Absorption", Marcel Dekker Inc., New York, 2000, pp. 155-181). Sodium taurocholate (NaTC) solutions are prepared at 3 Millimole (mM) and 15 mM, corresponding to fasted and fed gastrointestinal tract (GIT) states as described by Dressman J. B. For liquid excipients, the maximum capsule volume is assumed to be 0.6 Milliliter (mL) for a GIT volume of 250 mL, the calculated excipient concentration is 0.24% v/v. Hence, 1-methyl-2-pyrrolidone (NMP), propylene glycol (PG), and polyethylene glycol 400 (PEG400), excipient solutions of 0.24%, 1%, 5% v/v are assessed. 2-Hydroxypropyl-b-cyclodextrin (HP-b-CD) solutions are assessed in a similar concentration of 0.24% and 1% w/v. In all, counting the excipient-free buffer solutions, 15 different solutions are assessed with the eight drug molecules for the effect on PAMPA, resulting in 120 drug-excipient combinations.

With respect to the $pK_a$ measurement, the instruments potentiometric Gemini from the company pION, GLpKa from the company Sirius Analytical Instruments UK (Sirius), UV-metric D-PAS from Sirius, and SGA from Sirius are used to determine precision ionization constants. With the mentioned sparingly soluble compounds, several strategies are tried to overcome experimental difficulties, including the use of dimethyl sulfoxide (DMSO) and methanol as cosolvents. In the Gemini instrument, it is possible to determine the $pK_a$ even if there is precipitation during a portion of the titration, in either aqueous or cosolvent solutions. This is because the instrument can determine solubility and ionization constants simultaneously in the same titration. Furthermore, pH electrode calibration can be performed "in situ" by the Gemini instrument, concurrently with the $pK_a$ determination. This is especially an important feature for determinations in cosolvent solutions when the $pK_a$ is outside of the 4 to 9 range. This can be a substantial improvement in comparison to the traditional procedure of first doing a "blank" titration to determine the four Avdeef-Bucher pH electrode parameters (Avdeef, A. et al., "Accurate measurements of the concentration of hydrogen ions with a glass electrode: calibrations using the Prideaux and other universal buffer solutions and a computer-controlled automatic titrator", Anal. Chem., 1978, 50, 2137-2142).

In the example of permeability measurement described herein the artificial membrane permeability assay (PAMPA) method is applied. For that purpose, the PAMPA Evolution instrument from the company pION INC (Woburn, Mass., USA) is used, with data collected at room temperature (25±2° C.). The PAMPA 96-well "sandwich" is preloaded with 96 magnetic stirrers from the company pION (PN 110212). The typical sample concentrations are about 50 µM in the excipient-containing buffer solutions. The residual DMSO in these solutions is 0.5% v/v. The effective permeability, $P_e$, of each compound is measured in the pH 3 to pH 10 domain. The donor solutions are varied in pH (NaOH-treated universal buffer), while the receiver solutions have the same pH 7.4. Optimized pH-gradient conditions are selected, using the pOD procedure (Ruell J. A. et al., "PAMPA—a drug absorption in vitro model", 5, "Unstirred water layer in iso-pH mapping assays and $pK_a^{flux}$-optimized design (pOD-PAMPA)", Eur. J. Pharm. Sci., 2003, 20, 393-402), to ensure that the pH values will be above and below the $pK_a^{flux}$ value (defined below) of the compounds. The pH variation is necessary in order to correct the effective permeability values for ionization and absorption boundary layer (ABL) effects (Avdeef A., "Absorption and Drug Development", Wiley-Interscience, 2003, pp. 116-246; Avdeef A. et al., "S. Caco-2 permeability of weakly basic drugs predicted with the Double-Sink PAMPA $pK_a^{flux}$ method", Eur. J. Pharm. Sci., 2005, 24, 333-349; and Avdeef A. et al., "PAMPA—a drug absorption in vitro model", 11, "Matching the in vivo aqueous boundary layer by individual-well stirring in microtitre plates", Eur J. Pharm. Chem., 2004, 22, 365-374). The receiver solutions contain a surfactant mixture ("lipophilic sink") to mimic some of the function of drug-binding proteins (Avdeef A. et al., "High-throughput measurements of permeability profiles" in: van de Waterbeemd H. et al., "Drug Bioavailability. Estimation of Solubility, Permeability, Absorption and Bioavailability", Wiley-VCH: Weinheim, 2002, pp. 46-71). Vigorous stirring is employed in the assay, with stirring speed set to produce an aqueous boundary layer (ABL) thickness about 40 µm, to match the ABL contribution of the measured permeability to that expected in the GIT (Avdeef A. et al., "PAMPA—a drug absorption in vitro model", 11, "Matching the in vivo aqueous boundary layer by individual-well stirring in microtitre plates", Eur J. Pharm. Chem., 2004, 22, 365-374). The PAMPA sandwich is assembled and allowed to incubate for 30 minutes for the highly permeable molecules, in a controlled-environment chamber, for example the Gut-Box™ from the company pION (PN 110205) with a built-in magnetic stirring mechanism. The sandwich is then separated, and both the donor and receiver wells are assayed for the amount of material present, by comparison with the UV spectrum (230 nm to 500 nm) obtained from reference standard solutions. Mass balance is used to determine the amount of material remaining in the membrane filter (% R) and attached to the plastic walls of the microtitre plate (Avdeef A., "Absorption and Drug Development", Wiley-Interscience, 2003, pp. 116-246).

The effective permeability ($P_e$) is calculated as described previously, except that the usable filter area, 0.3 cm², is multiplied by the apparent porosity, 0.76. This latter step ensures that the ABL thickness determined from PAMPA assays using filters with a different porosity will be on an absolute scale (Nielsen P. E. et al., "PAMPA—a drug absorption in vitro model", 8, "Apparent filter porosity and the aqueous boundary layer", Eur. J. Pharm. Sci., 2004, 22, 33-41).

In the GIT epithelial environment, the ABL thickness is expected to be 30-100 µm, whereas in unstirred PAMPA, the ABL thickness can be as high as 4000 µm (Avdeef A. et al., "S. Caco-2 permeability of weakly basic drugs predicted with the Double-Sink PAMPA $pK_a^{flux}$ method", Eur. J. Pharm. Sci., 2005, 24, 333-349; Avdeef A. et al., "PAMPA—a drug absorption in vitro model", 11, "Matching the in vivo aqueous boundary layer by individual-well stirring in microtitre plates", Eur J. Pharm. Chem., 2004, 22, 365-374). By taking PAMPA (stirred or unstirred) data over a range of pH, it is possible to match the effect of the ABL to that expected for the GIT, by applying the $pK_a^{flux}$ method (Avdeef A., "Absorption and Drug Development", Wiley-Interscience, 2003, pp. 116-246; and Avdeef A. et al., "S. Caco-2 permeability of weakly basic drugs predicted with the Double-Sink PAMPA $pK_a^{flux}$ method", Eur. J. Pharm. Sci., 2005, 24, 333-349), briefly described below.

The effective permeability coefficient, $P_e$, is related to the membrane and ABL permeability coefficients, $P_m$ and $P_{ABL}$, respectively, as $$1/P_e = 1/P_{ABL} + 1/P_m \qquad (9)$$

For ionizable molecules, the membrane permeability, $P_m$, depends on pH of the bulk aqueous solution. The maximum possible $P_m$ is designated $P_o$, the intrinsic permeability of the uncharged species. For monoprotic weak acids and bases, the relationship between $P_m$ and $P_o$ may be stated in terms of the fraction of the uncharged species, $f_o$, as $$P_m = P_o f_o \tag{10}$$
$$= P_o / (10^{\pm(pH-pKa)} + 1)$$

with '+' used for acids, and '−' used for bases. Other cases are described elsewhere. Combining equations (9) and (10) leads to $$\frac{1}{P_e} = \frac{1}{P_{ABL}} + \frac{10^{\pm(pH-pK_a)}+1}{P_o} \tag{11}$$

ABL-limited transport is often observed for highly-permeable molecules, when $P_o \geqq P_{ABL}$. This is generally observed with lipophilic drugs, where the same $P_e$ is measured (about $30 \times 10^{-6}$ cm/s), regardless of the molecules, indicating a property of water rather than membrane. Equation (11) reduces to the logarithmic form (Avdeef A. et al., "S. Caco-2 permeability of weakly basic drugs predicted with the Double-Sink PAMPA $pK_a^{flux}$ method", Eur. J. Pharm. Sci., 2005, 24, 333-349)

$$\log P_e = \log P_e^{max} - \log(10^{\pm(pH-pK_a^{flux})}+1) \tag{12}$$

The maximum possible effective (measured) permeability, $P_e^{max}$, is defined as $$\log P_e^{max} = \log P_{ABL} - \log(1+P_{ABL}/P_o) \tag{13}$$

When $P_o \gg P_{ABL}$ (highly permeable molecules), $P_e^{max} \approx P_{ABL}$, indicating water rather than membrane diffusion. The "flux" ionization constant, $pK_a^{flux}$, refers to the pH value where the resistance to transport across a permeation barrier is 50% due to the ABL and 50% due to the membrane.

With respect to the results of the exemplary permeability measurement described herein and their interpretation, FIG. 1 shows a comparison of the ionization constants determined by the various "state-of-the-art" approaches used. Since all of the compounds are only sparingly soluble in water, cosolvents are used, and the aqueous values are extrapolated by the Yasuda-Shedlovsky (Avdeef A. et al., "pH-metric log P", 3, "Glass electrode calibration in methanol-water, applied to $pK_a$ determination of water-insoluble substances", Anal. Chem., 1993, 65, 42-49) approach in the case of GLpKa and D-PAS instruments, and by linear extrapolation to zero wt % cosolvent in the case of the Gemini instrument. The commercially configured SGA instrument currently does not have a cosolvent capability, so only aqueous universal buffers are used. Since the D-PAS and SGA instruments are UV-based, it is possible to use lower concentration solutions in the $pK_a$ determination, avoiding some, but not all, of the problems of low aqueous solubility. Two of the most popularly used cosolvents are employed in this exemplary permeability measurement: DMSO and methanol. In just about all of the cases, the DMSO extrapolated $pK_a$ values are systematically lower than those extrapolated from methanol-water mixtures, following the trend, $pK_a^{DMSO} = 0.61 + 0.86\ pK_a^{CH3OH}$ ($r^2 = 0.99$, $s = 0.27$, $n = 8$). Since butacaine and astemizole are diprotic bases, it is actually possible to determine the low-pH $pK_a$ in the absence of cosolvent. In both cases, the DMSO extrapolated values are more biased than those of methanol. The variance is particularly evident in the case of butacaine low pH $pK_a$ value. The methanol extrapolated values seem to be more accurate in general, a conclusion supported by methanol being viewed as the "least problematic" of the cosolvents used in $pK_a$ determinations. With DMSO results excluded, in this exemplary permeability measurement it is not to relied on the SGA values, since cosolvent use was not an available feature, and since the deviations from the identity line in FIG. 1 are substantial. FIG. 1 reveals that best concordance is seen between potentiometric GLpKa and Gemini values, as indicated by the filled circles being closest to the identity line.

The GLpKa and Gemini values can be simply averaged for the working set. In this exemplary permeability measurement, that is not done for the following reason: inspite of well designed assays, where the cosolvent-water ratios are picked to be sufficiently high to avoid precipitation, it is nearly impossible to be certain that precipitation does not occur at the lowest cosolvent-water ratios. Due to the design of the sample changer in the GLpKa, it is not convenient to view the solutions during the titration. In contrast, the Gemini has the glass vial in clear view. Visual observations suggested that it was highly probable that in a number of cases, some precipitation must have taken place in the GLpKa with these low solubility compounds. Furthermore, the Gemini electrode calibration procedure made the $pK_a$ values less than 3 more reliable in cosolvent solutions.

Figure 2:
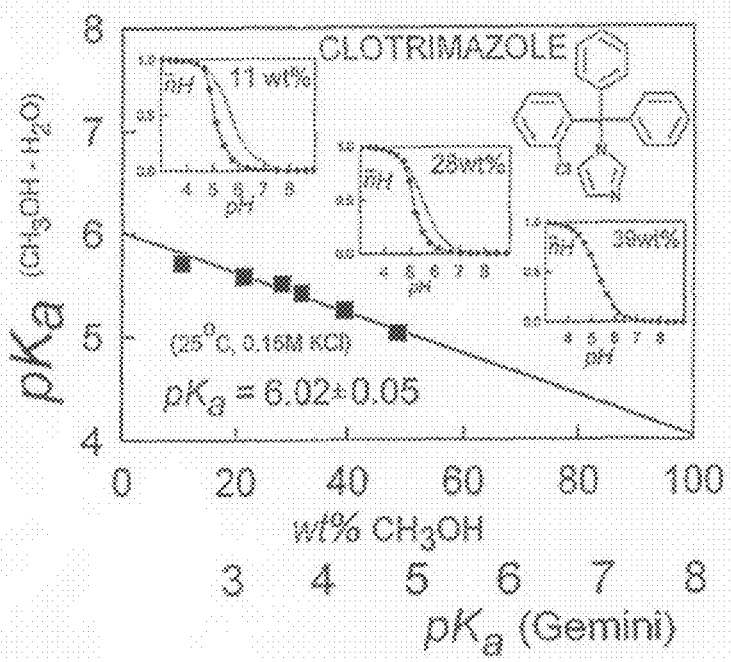
FIG. 2 shows linear extrapolation of apparent $pK_a$ determined in various mixtures of methanol-water of the method from FIG. 1.

FIG. 2 relates to the Gemini results of $pK_a$ measurements. It illustrates what can conceivably go wrong with conventionally designed assays, and the usual consequences in conventional measurements, which by contrast are circumcalculated by the Gemini. Illustrated in FIG. 2 are six determinations of the clotrimazole $pK_a$ in 11-49 wt % methanol. The zero-cosolvent extrapolated $pK_a$ is $6.02 \pm 0.05$. The insets in FIG. 2 are Bjerrum plots (Avdeef A. "Absorption and Drug Development", Wiley-Interscience, 2003, pp. 116-246) for the 11, 28, and 39 wt % titrations. The dashed curves in the insets correspond to the expected curves in the limit of infinitely low concentration of sample, where no precipitation would take place. The solid curves, linking the measured points indicate a significant displacement from the precipitation free dashed curves. This displacement takes place because clotrimazole precipitated in titrations below 35 wt % methanol. Conventional refinement programs, not taking such precipitation into effect, would systematically underestimate the $pK_a$ with decreasing cosolvent ratios, with an error as high as a log unit in the case of 11 wt % (FIG. 2 inset). If the biased values are the basis of extrapolation, the $pK_a$ would be near 5, a log unit off (data not shown).

The unique aspect of the refinement program in the Gemini instrument is that it can determine the unbiased $pK_a$ value in the presence of some precipitation, since the solubility and the $pK_a$ values are simultaneously refined. The fit in FIG. 2 is weighted by the errors obtained in the individual-set refinements, which down-weighs the contributions of the lowest wt % cosolvent points, if "too much" precipitation prevents a precise determination of the $pK_a$ value.

The novel $pK_a$ technology is best suited for determining the ionization constants of the most insoluble compounds. The following improvements are evident: (a) a wider span of cosolvent ratios is feasible, since precipitation at the lower ratios is circumcalculated, (b) higher concentrations of sample may be used, for more sensitive determination, (c) selecting the "best" cosolvent ratios is less critical to the extrapolation process, making the method more "fault" tolerant, and (d) in situ pH electrode calibration makes $pK_a$ determinations in a wider pH window possible in cosolvent titrations.

In Table 1 (see above) the Gemini-determined $pK_a$ values at 0.15 M (KCl) ionic strength are listed. These values are converted to 0.01 M ionic strength level and used in all of the subsequent PAMPA analyses, since the permeability buffer is at the lower ionic strength. In the case of 0.1 and 0.2 M KCl, appropriate adjustments to the constant were made (Avdeef A., "Absorption and Drug Development", Wiley-Interscience, 2003, pp. 116-246).

Figure 3:
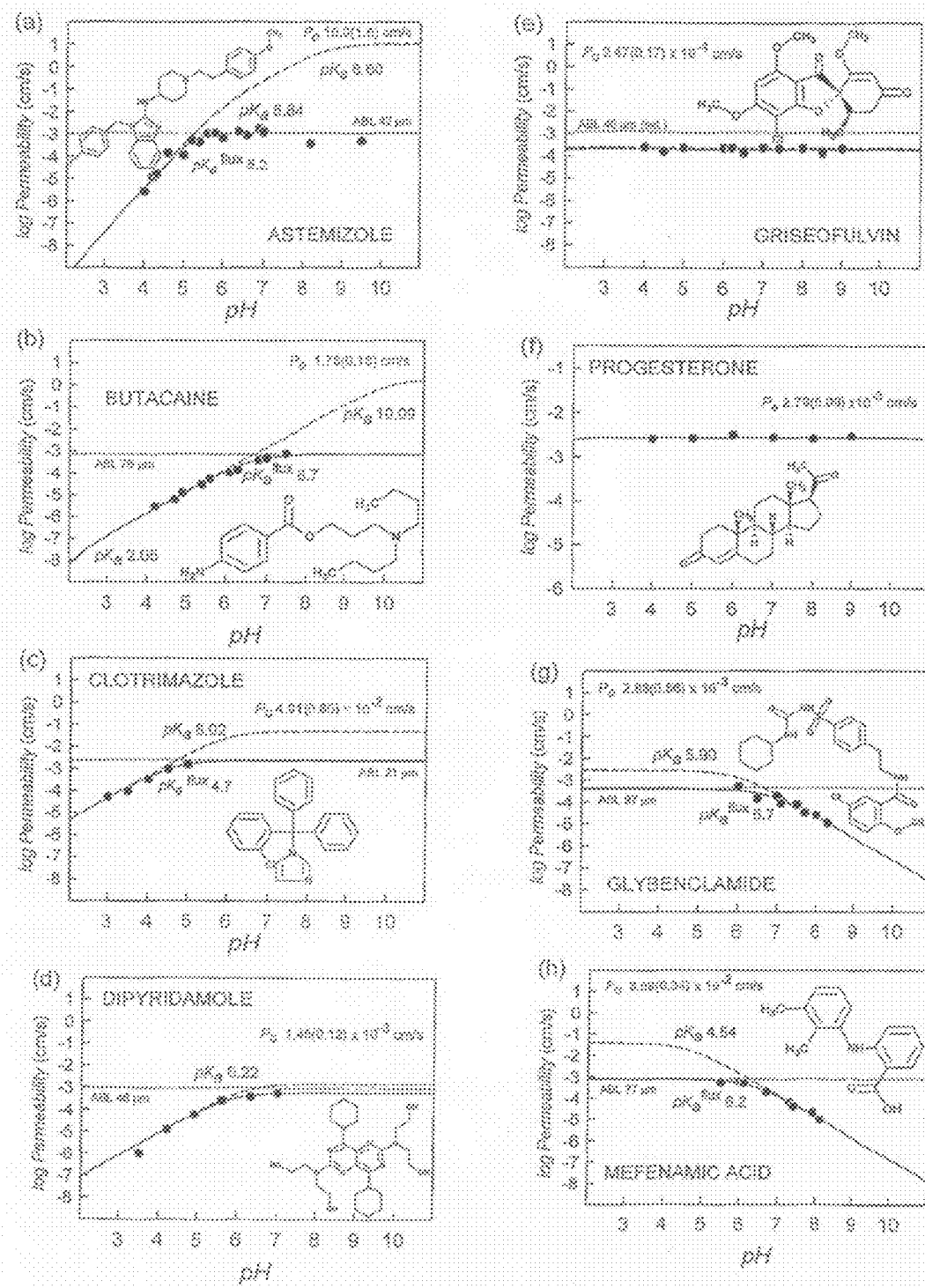
FIG. 3 shows log permeability vs. pH plots of the eight compounds measured in the example of permeability measurements of the method from FIG. 1.

FIG. 3 relates to PAMPA measurements without excipients. It shows the excipient-free permeability profiles for the mentioned molecules. Solid lines indicate the best fit of the effective permeability values, log $P_e$ (filled circles), as a function of pH, according to equation (12). Sample values of $pK_a^{flux}$ are indicated in FIG. 3 (a-c,g,h). The dashed-line membrane permeability curves, log $P_m$ vs. pH, result when the calculated aqueous boundary layer (ABL) permeability values (dotted horizontal lines) are factored out of the effective permeability values (equations (9) and (10)). The solid-line curves in FIG. 3 (all, except (d) and (e)) are examples of ABL limited transport, since at their maximum extent, they are below the dashed-line curves. With bases, for $pH \gg pK_a^{flux}$, equation (12) is that of a horizontal line, and for $pH \ll pK_a^{flux}$, equation (12) is that of a diagonal line, with a slope of +1. With acids, for $pH \ll pK_a^{flux}$, equation (12) is that of a horizontal line, and for $pH \gg pK_a^{flux}$, equation (12) is that of a diagonal line, with a slope of −1.

All of the permeability data are measured with the Gut-Box setting at 40 μm ABL, except for progesterone, where the setting is at 25 μm ABL, since the direct $pK_a^{flux}$ method cannot be used with nonionizable molecules. For such molecules, a calibration procedure is known (Avdeef A. et al., "Caco-2 permeability of weakly basic drugs predicted with the Double-Sink PAMPA $pK_a^{flux}$ method", Eur. J. Pharm. Sci., 2005, 24, 333-349; and Avdeef A. et al., "PAMPA—a drug absorption in vitro model", 11, "Matching the in vivo aqueous boundary layer by individual-well stirring in microtitre plates", Eur J. Pharm. Chem., 2004, 22, 365-374). The refined ABL thicknesses (equation (12)) are indicated in FIG. 3, and range from 21-97 μm. The three values exceeding 75 μm may indicate that butacaine, mefenamic acid, and glybenclamide are aggregated in solution. Since ABL permeability depends on molecular weight of the species diffusing in aqueous solution, the use of the monomer molecular weight in calculations leads to an increased apparent ABL thickness.

With respect to PAMPA measurements with excipients, over 1200 double sink PAMPA measurements are performed in the pH range 3-10. High precision $pK_a$s (Gemini) are used for the $pK_a^{flux}$ method to calculate the intrinsic and ABL permeability. Table 2 compiles the 120 $P_o$ values determined in this exemplary permeability measurement, along with the maximum membrane retention (% R), and apparent ABL thicknesses.

griseofulvin, with $P_o$ values ranging from $1.8 \times 10^{-4}$ (5% v/v PG) to $4.1 \times 10^{-4}$ cm/s (0.1 M KCl).

Membrane retention is substantial in most molecules, with astemizole ranking the highest, with values in the range 79%-90% typically (but dropping to 24% in the case of 15 mM NaTC). Inspite of such depletions from the aqueous phases, it is still possible to access permeability of astemizole by PAMPA Evolution instrument software. As indicated in Table 2, the other retained molecules change in ranking with the excipients. Low membrane retentions indicate that the excipient competes effectively with the PAMPA membrane in holding on to the compounds, as for example in the case of 15 mM NaTC, particularly for clotrimazole, where retention drops to 4%, compared to the excipient free value of 80%.

The ABL thicknesses listed in Table 2 are also indicative of excipient-drug interactions. Ideally, if the drugs formed neither aggregates in excipient-free solutions, nor associated complexes with excipients, then the determined ABL thicknesses, $h_{ABL}$, should have been about 40 μm (or 25 μm in the case of the highly-stirred progesterone solutions). In a number of cases, such as with astemizole and clotrimazole, the expected $h_{ABL} < 50$ μm are determined. However, in stark contrast, the calculated ABL thicknesses in 15 mM NaTC solutions are over 1000 μm in a number of cases. Table 2 lists the theoretically expected and the experimental $P_{ABL}$. The lowered observed values can be interpreted to arise from the effect of associated complexes which have very high molecular weights. The relationship between $P_{ABL}$ and MW is known in the art. For example, if equation 4 from Avdeef A., "The Rise of PAMPA", Expert Opin. Drug Metab. Toxicol., 2005, 1, 325-342 is applied to the apparent $P_{ABL}$, the excipient free solutions (0% NaTC, Table 3) appear to indicate aqueous diffusion of monomers in the case of astemizole, clotrimazole, and dipyridamole, since the ratio of the apparent molecular weight, MW*(based on the assumption of 40 μm ABL) to the true molecular weight, MW*/MW, is close to 1. In the same buffer solutions, aggregates or the order of 4-7 seem to be indicated for some of the other low-solubility drugs (Streng W. H. et al., "Determination of solution aggregation using solubility, conductivity, calorimetry, and pH measurements", Int. J. Pharm., 1996, 135, 43-52). In 3 mM sodium taurocholate solutions, only dipyridamole appears to behave as a monomer, with the other molecules appearing as aggregates of order 3-5. These aggregates can be associations between drug and excipient. In 15 mM NaTC solutions, the reduction in the ABL permeability is extreme, and simplistic analysis indicated aggregation orders as high as 56000, which does not seem reasonable. It is difficult to be very certain that complexation with the excipient is the only explanation, since

TABLE 2

| COMPOUND | MW | $P_{ABL}$ expected (Ref. Xx) | $P_{ABL}$ 0 mM NaTC | $P_{ABL}$ 3 mM NaTC | $P_{ABL}$ 15 mM NaTC | MW*/MW |
|---|---|---|---|---|---|---|
| astemizole | 458.6 | 1135 | 1080 | 561 | 9 | 1, 5, 56000 |
| butacaine | 306.4 | 1360 | 713 | 954 | 13 | 4, 2, 30000 |
| clotrimazole | 344.8 | 1290 | 2400 | 604 | — | <1, 5, — |
| dipyridamole | 504.6 | 1088 | 941 | 922 | 47 | 1, 1, 1100 |
| glybenclamide | 494.0 | 1098 | 451 | — | 12 | 7, —, 24000 |
| mefenamic acid | 241.3 | 1514 | 782 | 909 | 795 | 4, 3, 4 |

The most permeable molecule is astemizole, with $P_o$ values ranging from 0.5 (0.24% v/v PEG400 and 15 mM NaTC) to 32 cm/s (3 mM NaTC). The least permeable molecule is 15 mM NaTC solutions are hard to work with in the robotic instrument, due to the easy formation of bubbles in the microtitre plate. The possibility that 15 mM NaTC solution is dissolving some of the PAMPA membrane is of concern, but no visual evidence of the effect (turbidity in solution) are observed.

Figure 4:
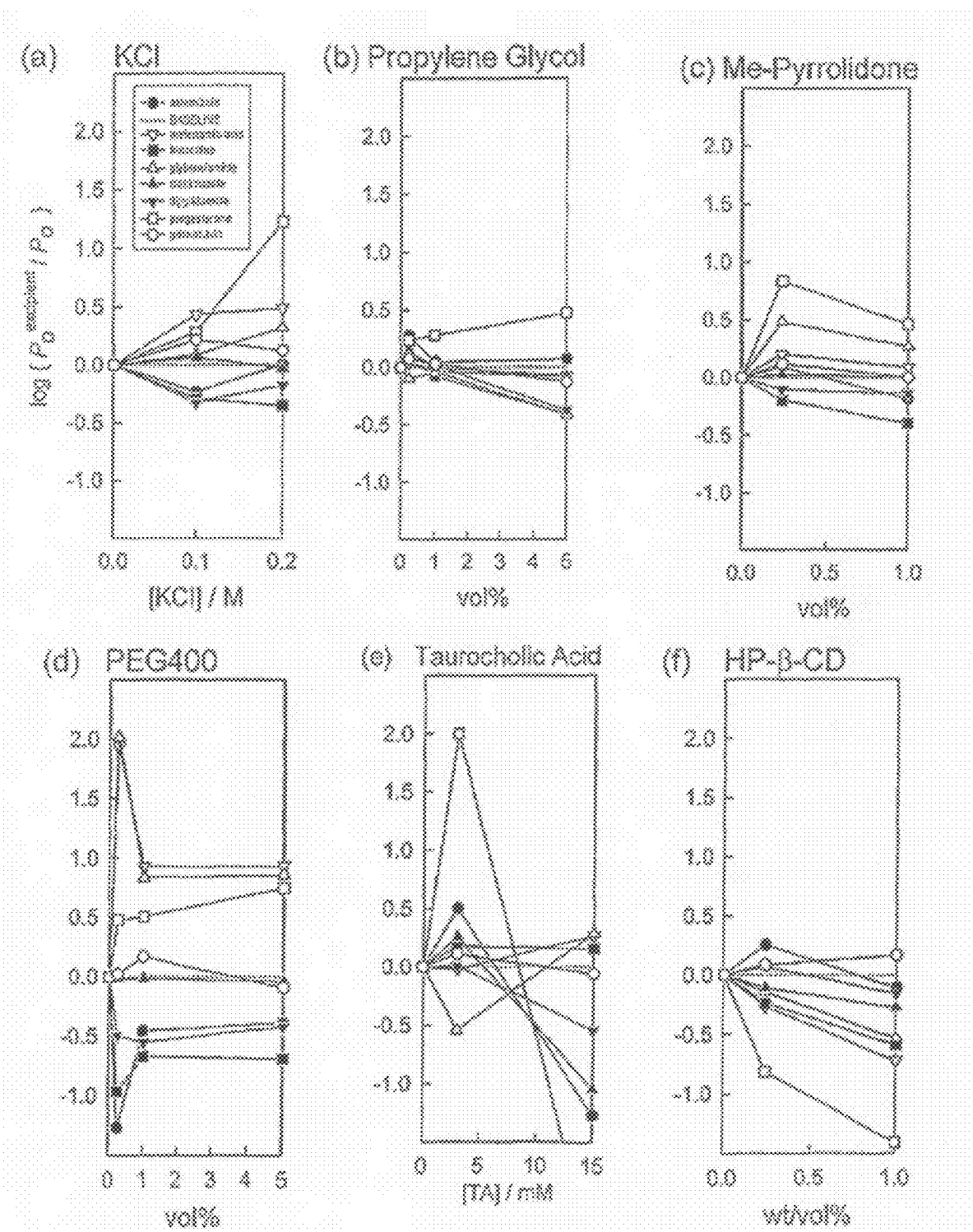
FIG. 4 shows plots of the differences between log intrinsic permeability in the presence of excipients and log intrinsic permeability in the absence of excipients, as a function of the quantity of excipients of the example of permeability measurements of the method from FIG. 1.

FIG. 4 plots the differences between log $P_o$ in excipient-containing solutions and those of excipient-free (base level) solutions, as a function of the amount of excipient. In many cases, it is evident that bases behave differently from acids and neutrals. In KCl, NMP, and PEG400 solutions, bases appear to have lowered intrinsic permeabilities in the presence of excipients, whiles acids and neutrals have elevated permeabilities. For NaTC and HP-β-CD containing solutions, at the highest level of excipient, all compounds appear to have diminished permeability. Apparently, the binding of drugs to such excipients is sufficiently strong, that the remaining free fraction of the unbound drug concentrations drop significantly, so that the concentration gradient between the donor and acceptor compartments in the permeation cell decreases, leading to decreased permeability.

Figure 5:
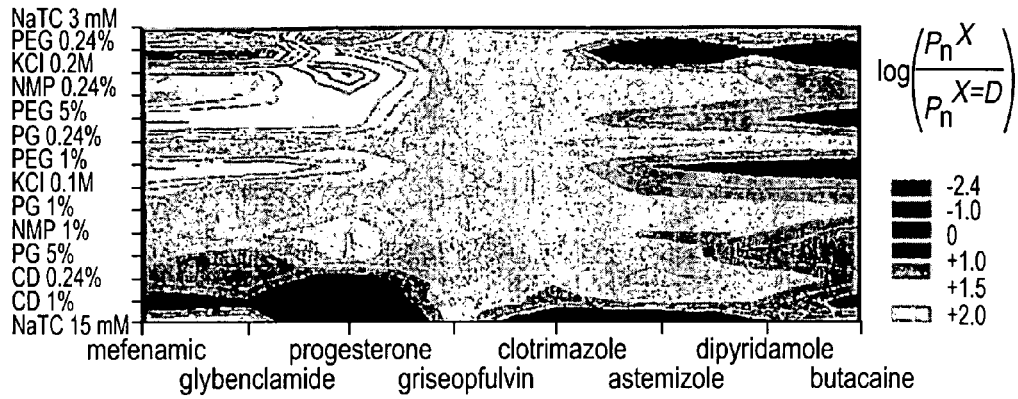
FIG. 5 shows a PAMPA-Mapping scheme based on log intrinsic permeability for the example of permeability measurements of the method from FIG. 1.
Figure 6:
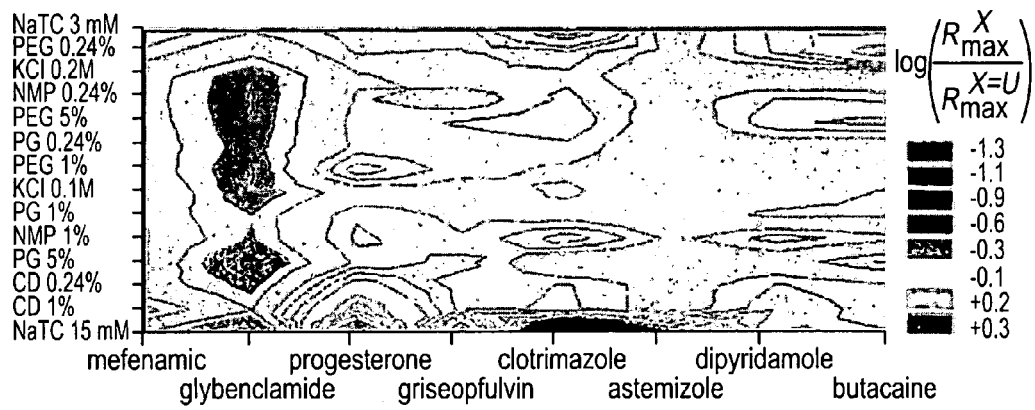
FIG. 6 shows a PAMPA-Mapping scheme based on log membrane retention for the example of permeability measurements of the method from FIG. 1.
Figure 7:
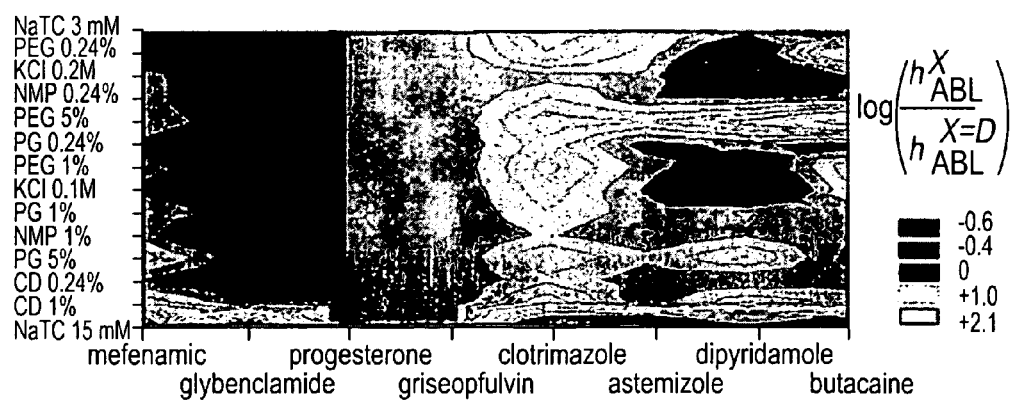
FIG. 7 shows a PAMPA-Mapping scheme based on log aqueous boundary layer for the example of permeability measurements of the method from FIG. 1.

With respect to visualization of the results of the exemplary permeability measurement described herein, although FIG. 4 describes the effect of the excipients, it is visually difficult to grasp quickly and use in practical decision making regarding the uses of excipients. Therefore, a mapping scheme is shown in FIG. 5, FIG. 6, and FIG. 7, called PAMPA-Mapping, which improves the visual aspects of the excipient effects. Shown are three component maps of PAMPA-Mapping: permeability (FIG. 5), membrane retention (FIG. 6), and ABL (FIG. 7). Along the vertical axes are the excipient compositions, rank ordered by their enhancement effect on intrinsic permeability. Along the horizontal axes are the drugs, arranged in the order of most enhanced to least enhanced permeability. On the average across all excipients, the intrinsic permeability of acids and neutrals is enhanced, but depressed for the bases. The warm colors, which are red, yellow and the like indicate an increase in the property mapped as a result of an excipient, where the base level is defined by excipient-free results. The cool colors, which are blue violet and the like, indicate the opposite. For example, if the design objective is to enhance permeability, the top left corner of the permeability map identifies the molecules and excipient combinations that are most promising in increasing permeability, and the bottom right corner of the map reveals regions that may be most problematic.

The membrane retention map of FIG. 6 is redundant to the permeability map of FIG. 5, to an extent. If simplistic Fick's laws of diffusion were solely responsible for transport, then the two maps should be the same in principle. However, it can be seen that there are subtle differences between the two maps. A consideration for explaining this effect is that when retention increases severely, there is too little compound for analytical detection. In none of the cases considered herein that is a problem. The absence of the Double-Sink scavenger in the receiver compartments, seems that the membrane retention map indicates insurmountable analytical problems for the UV detection method used in the PAMPA Evolution instrument.

The ABL map of FIG. 7 is roughly a mirror image of the other two maps of FIG. 5 and FIG. 6. The elevated $h_{ABL}$ ratios may be interpreted to mean high drug-excipient interaction, leading to slower diffusion in the aqueous layer and decreased membrane retention. An unexpected interpretation of the ABL map may be that some drugs form aggregates in excipient free solutions (see above), but in the presence of certain excipients, the tendency for the drugs to self-associate is lessened. This can be the case with glybenclamide, butacaine and dipyridamole in KCl, 0.24% v/v PG, 1% v/v NMP, and 1% PEG, for example, as indicated by deep-blue regions in the map.

The color maps introduced are new and their use is continually evolving. The maps look systematic in appearance, partly because the excipients and compounds were rank ordered in an optimal way. With a large number of molecules, and perhaps more conditions and types of excipients, in silico algorithms could be developed, where the maps "self-organize" by some sort of similarity schemes.

Appropriate solubility measurement for the first embodiment of the method according to the invention can also be performed in various manner. Since many molecules can have very low solubility, particularly molecules from discovery programs, measurement of solubility needs to be both rapid and compound-sparing. Screening for excipient effects on solubility makes the task further daunting. Nevertheless, rapid methods of systematic screening for solubilizing agents are emerging. Chen et al. (Chen, H. et al., "A high-throughput combinatorial approach for the discovery of a Cremophor EL-free paclitaxel formulation", Pharm. Res., 2003, 20, 1302-1308) uses full factorial robotic assay to screen about 10,000 combinations of twelve excipients (including PEG400, polysorbate 80, and ethanol) in a number of combinations to discover an improved Cremophor EL free formulation for paclitaxel, a well established marketed drug. There clearly are opportunities to improve both the efficiency and the accuracy of such rapid methods, using partial factorial design-of-experiments (DOE). Commercial software linking DOE approaches directly to robotic control exist in the art. Also, there are opportunities to automate computational methods to properly treat the solubility data for possible aggregation effects.

In the exemplary solubility-excipient measurement described herein, the theme explored in a Double-Sink PAMPA excipient, where the method of PAMPA-Mapping is introduced, bases on eight sparingly soluble drugs (astemizole, butacaine, clotrimazole, dipyridamole, griseofulvin, progesterone, glybenclamide, and mefenemic acid), measured under fifteen combinations of six excipients (sodium taurocholate, 2-hydroxypropyl-β-cyclodextrin, potassium chloride, propylene glycol, 1-methyl-2-pyrrolidone, and polyethylene glycol 400).

The mentioned example of solubility measurement is performed using the compounds astemizole, butacaine, clotrimazole, dipyridamole, griseofulvin, progesterone, glybenclamide, and mefenamic acid. The pH of the assayed donor solutions is adjusted with universal buffers from the company pION (PN 100621, 1100151).

Excipients used in this example of solubility measurement comprise quantities of six excipients which are selected to overlap the concentrations expected in the gastrointestinal fluid under clinically relevant conditions. Briefly, KCl was selected at 0.1 and 0.2 M; sodium taurocholate (NaTC) solutions are prepared at 3 and 15 mM, corresponding to fasted and fed GIT states (35). For liquid excipients, the maximum capsule volume is assumed to be 0.6 mL: for a GIT volume of 250 mL (35), the calculated excipient concentration is 0.24% v/v. Hence, for N-methylpyrrilidone (NMP), propylene glycol (PG), and polyethylene glycol 400 (PEG400), excipient solutions of 0.24, 1, and 5% v/v are tested. With encapsulated solid excipients, such as hydroxypropyl-β-cyclodextrin (HP-β-CD), with MW 1396 and solubility 450 mg/mL, it should be possible to pack 270 mg into a 0.6 mL capsule, which is equivalent to a 0.1% w/v solution in the GIT volume. Slightly higher values of 0.24 and 1% w/v are used in this example of solubility measurement. In all, counting the excipient-free buffer solutions, 15 different solutions are tested with the eight drug molecules for the effect on solubility, resulting in 120 drug-excipient combinations.

With respect to the $pK_a$ measurement, the high-precision $pK_a$ data, determined by the potentiometric method using the Gemini instrument of the company pION, are determined by extrapolation in methanol-water solutions, taking advantage of the Gemini's capability to determine $pK_a$ values even if there is precipitation during a portion of the titration, in either aqueous or cosolvent solutions. The pH electrode calibration was performed in situ by the instrument, concurrently with the $pK_a$ determination, especially an important feature for $pK_a<3$ or $pK_a>10$ in cosolvent solutions.

The highly-automated direct-UV 96-well microtitre plate equilibrium solubility method implemented in the μSOL Evolution instrument from the company pION INC (Woburn, Mass., USA) is used in this example of solubility measurement, with data collected at room temperature (25±2° C.). Samples are typically introduced as 10-30 mM DMSO solutions. The robotic liquid handling system (e.g. Beckman Coulter Biomek-FX ADMETox Workstation) draws a 3-10 μL aliquot of the DMSO stock solution and mixes it into an aqueous universal buffer solution, so that the final (maximum) sample concentration is 50-250 μM in the excipient containing buffer solutions. The residual DMSO concentration is kept at 1.0% (v/v) in the final buffer solutions. The solutions are varied in pH (NaOH-treated universal buffer). This is necessary in order to determine the aggregation and intrinsic solubility constants (Avdeef A. et al., "Dissolution-Solubility: pH, Buffer, Salt, Dual-Solid, and Aggregation Effects" in: Testa B. et al., "Comprehensive Medicinal Chemistry II, Vol. 5", ADME-TOX Approaches, Elsevier: Oxford, UK, 2006). Each solubility-pH measurement is performed in duplicate, and the results are averaged by the instrument software. The buffers used in the assay are automatically prepared by the robotic system. The quality controls of the buffers and the pH electrode are performed by alkalimetric titration, incorporating the Avdeef-Bucher (Avdeef, A. et al., "Accurate measurements of the concentration of hydrogen ions with a glass electrode: calibrations using the Prideaux and other universal buffer solutions and a computer-controlled automatic titrator", Anal. Chem., 1978, 50, 2137-2142) procedure. After 18±1 h, the buffer solutions containing suspensions of the drug solid are filtered (0.2 μm pore microfilter), and the supernatant solutions are assayed for the amount of material present, by comparison with the UV spectrum (230 to 500 nm) obtained from a reference standard, using a proprietary spectroscopic procedure that comes with the Evolution instrument.

Figure 8:
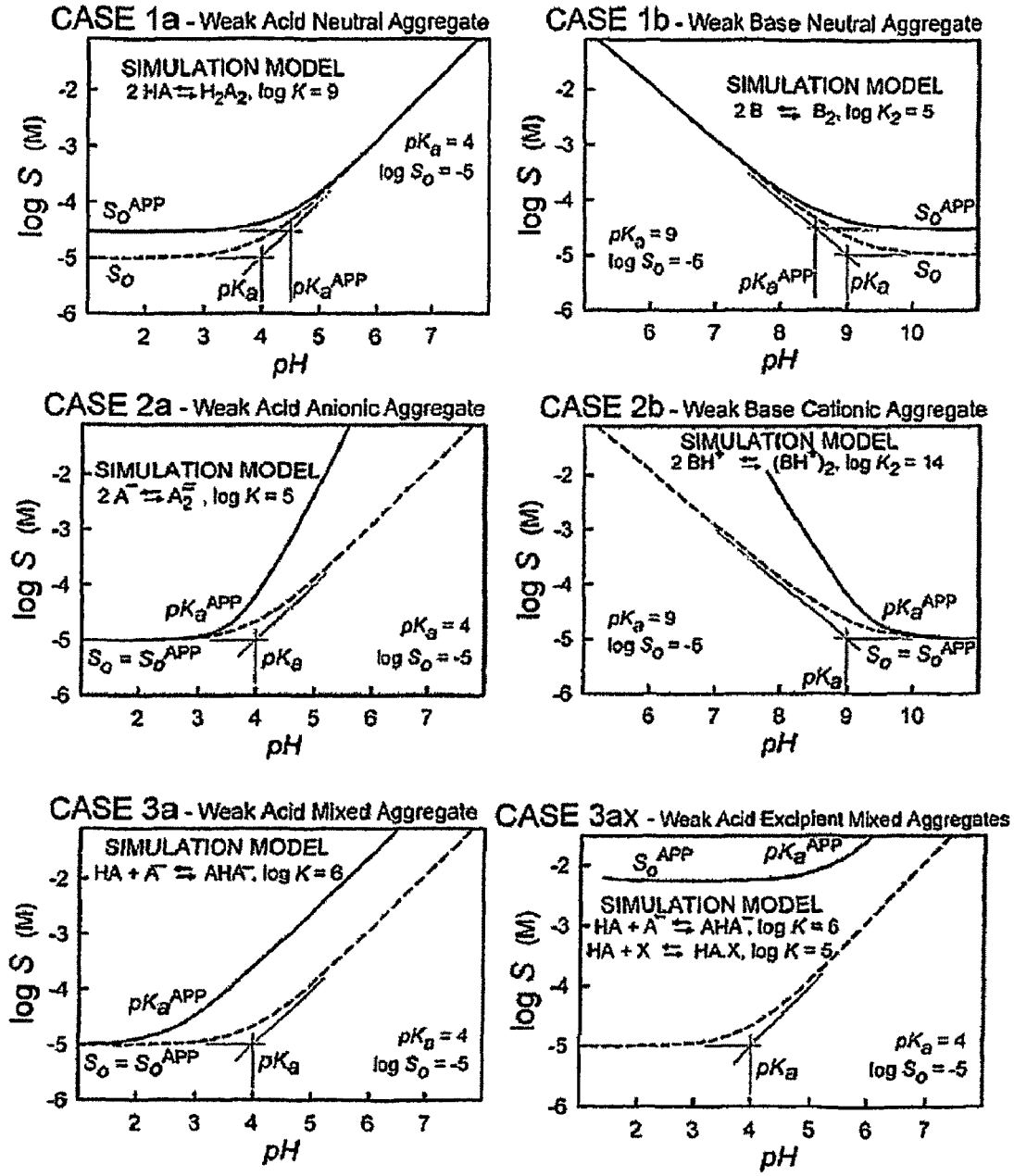
FIG. 8 shows six cases of aggregation reactions for a example of solubility measurements of the method from FIG. 1.

With respect to cases $1a$, $1b$, $2a$, and $2b$ of FIG. 8 it is to state that when a compound forms a dimer or a higher order oligomer in aqueous solution, the characteristic solubility-pH profile takes on a shape not predicted by the Henderson-Hasselbalch equation (cf., solid curves in FIG. 8), and often indicates an apparent $pK_a$ that is different from the true $pK_a$ (e.g., cases $1a$ and $1b$ in FIG. 8), as determined potentiometrically in dilute aqueous or cosolvent solutions (29). FIG. 8 shows six different cases of aggregation-induced distortions of log S-pH curves. Derivations of cases $1a$, $1b$, $2a$ and $2b$ are described in the literature, and methods to extract underlying intrinsic solubility values are known in the art. Cases $3a$ and $3ax$ treatments are new, and their derivations are briefly described hereinbelow. Based on such $pK_a$-shift in solubility analysis, dimerization constants ranging from $1.7 \times 10^{+3}$ to $1.8 \times 10^{+5}$ M$^{-1}$ are proposed (Avdeef A. et al., "Dissolution-Solubility: pH, Buffer, Salt, Dual-Solid, and Aggregation Effects" in: Testa B. et al., "Comprehensive Medicinal Chemistry II, Vol. 5 ADME-TOX Approaches", Elsevier: Oxford, UK, 2006) for phenazopyridine (case $2b$ in FIG. 8), indomethacin (case $2a$ in FIG. 8), 2-naphthoic acid (case $2a$ in FIG. 8), and piroxicam (case $1a$ in FIG. 8).

The equations underlying and summarizing this example of solubility measurement mathematically describe pH-solubility relationships, and can be used for the practical purpose of data interpolation, extrapolation, smoothing, and compaction. Furthermore, the $pK_a$-shift method can be used as a quick alert tool. As is implied, the molecule must have an ionization group within the accessible pH range, in order for the method to work. When a log S vs. pH plot is inspected, and the true $pK_a$ is known independently, it can be quickly surmised whether aggregates are present, and whether these "anomaly" effects are due to the neutral or the charged form of the drug. Moreover, the intrinsic solubility may be calculated from the magnitude or the direction of the $pK_a$ shift. These are the best uses of the shift method. Caution is needed not to mechanistically overinterpret the measurement data, however. If an uncharged molecule undergoes some speciation anomaly (aggregation, DMSO binding, filter retention, etc.), weak acids will indicate an apparent $pK_a$ higher than the true $pK_a$ (case $1a$ in FIG. 8), and weak bases will indicate an apparent $pK_a$ lower than the true $pK_a$ (case $1b$ in FIG. 8). If the observed shifts are opposite of what's stated above, then the charged (rather than the neutral) species is involved in the anomaly (cases $2a$ and $2b$ in FIG. 8). Although the precise mechanism of the anomaly may not be apparent in all cases, the shift combined with the apparent solubility will often reveal the intrinsic (unshifted) solubility, $S_o$. There is a further practical consequence to this with excipients: it is possible in many instances to measure solubility in the presence of excipients and at the same time to assess the solubility that would have been evident in the absence of added excipients, as though they were the source of anomaly.

Six types of aggregates, $(HA)_n$, $B_n$, $A_n^{n-}$, $(BH^+)_n$, $(AH \cdot A)_n^{n-}$, and $(AH \cdot A)_n^{n-}$, in the presence of excipients are considered. Their derivations follow along the lines reported in the literature. This is briefly summarized below for the two new situations:

In the first situation, mixed charge weak acid aggregates $(AH \cdot A)_n^{n-}$ are regarded (case $3a$ in FIG. 8). In Cases $2a$ and $2b$, the order of aggregation is revealed by slopes greater than one in the log S-pH plots (Avdeef A. et al., "Dissolution-Solubility: pH, Buffer, Salt, Dual-Solid, and Aggregation Effects" in: Testa B. et al. "Comprehensive Medicinal Chemistry II", Vol. 5 ADME-TOX Approaches, Elsevier: Oxford, UK, 2006). In this example of solubility measurement, several instances of slopes being near one are determined, even though some sort of aggregation is apparently taking place. There is a plausible model to describe this case. It can be hypothesized that the oligomeric mixed-charge weak acid species, $(AH \cdot A)_n^{n-}$, forms, which contains a 1:1 ratio of HA and $A^-$. The required equilibrium equations and the associated concentration quotients to completely define the mass balance problem are $$HA \rightleftharpoons H^+ + A^- \quad K_a = [H^+][A^-]/[HA] \tag{14}$$

$$HA(s) \rightleftharpoons HA \quad S_0 = [HA] \tag{15}$$

$$nA^- + nHA \rightleftharpoons (AH \cdot A)_n^{n-} \quad K_n^* = [(AH \cdot A)_n^{n-}]/[HA]^n[A^-]^n \tag{16}$$

Solubility is defined by $$S = [A^-] + [HA] + 2n[(AH \cdot A)_n^{n-}] \tag{17}$$

The [A⁻] and [(AH·A)$_n^{n-}$] components in equation (17) may be expanded in terms of [HA], pH, and the various equilibrium constants:

$$S = [HA]K_a/[H^+] + [HA] + 2nK_n^*[A^-]^n[HA]^n \quad (18)$$

$$= [HA]\{K_a/[H^+] + 1 + 2nK_n^*K_a^n[HA]^{2n-1}/[H^+]^n\}$$

In logarithmic general form, $$\log S = \log S_o + \log(1 + K_a/[H^+] + 2nK_n^*K_a^nS_o^{2n-1}/[H^+]^n) \quad (19)$$

Two limiting forms of equation (19) may be posed as $$\log S = \log S_o @ pH \ll pK_a^{APP} \quad (20)$$

$$\log S = \log 2n + \log K_n^* + 2n \cdot \log S_o - npK_a + npH @ pH \gg pK_a \quad (21)$$

Equation (20) indicates that the formation of mixed-charge aggregates does not obscure the value of the intrinsic solubility in low pH solutions (case 3a in FIG. 8). If for a weak acid, whose apparent pK$_a$ in a saturated solution is less than the true pK$_a$, a slope of +1 for pH$\gg$pK$_a$ in a log S vs. pH plot is consistent with the formation of the dimeric species AH·A⁻. A slope of +2, however, could indicate a case 2a dimer or a case 3a tetramer, which may be difficult to discern.

In the second situation, mixed charge aggregates (AH·A)$_n^{n-}$ in presence of an excipient are regarded (case 3ax in FIG. 8). In case 3a, the slope in the log S-pH plot cannot be less than one. The cases observed where the slope is less than one needed further modification to computation models. One can hypothesize that the oligomeric mixed-charge weak acid species, (AH·A)$_n^{n-}$, forms, in the presence of an excipient, X, which binds only the neutral form of the weak acid HA. In addition to eqs. 1 and 2, one needs $$HA + X \rightleftharpoons AH \cdot X \quad K^{\boxtimes} = [AH \cdot X]/[HA] \quad (22)$$

The K$^{\boxtimes}$ equilibrium constant embeds the product of the equilibrium constant for reaction in equation (22) and the concentration of the excipient, X, which is assumed to be practically constant (i.e., [HA]$_{total}\ll$[X]$_{total}$).

Solubility is Defined by $$S = [A^-] + [HA] + 2n[(AH \cdot A)_n^{n-}] + [AH \cdot X] \quad (23)$$

As before, the non-[HA] components in equation (23) may be expanded in terms of [HA] and the various equilibrium constants, leading to the general form equation (equation (19)):

$$\log S = \log S_o + \log(1 + K_a/[H^+] + 2nK_n^*K_a^nS_o^{2n-1}/[H^+]^n + K^{\boxtimes}) \quad (24)$$

The case 3ax example in FIG. 8 is based equilibrium constants indicated in the figure. In general it is not possible to extract limiting forms of the equation, other than to suggest that the slope at extreme pH still needs to be n$\geq$1, because of the n-dependence of pH in equation (24). As the case 3ax example in FIG. 8 illustrates, if the measured data are only taken from the bend in the curve at high pH, the slope may appear less than one, but if higher-pH data were available, the model would predict a slope of +1.

With respect to refinement of the aggregation parameters described, solubility-pH data measured by the μSOL Evolution instrument are processed by the onboard software and stored in the ELM™ Data Manager from the company pION. The data from several different assays, pooled in ELM, are further tested by the software for the presence of aggregates. One of the equations is automatically selected by the Evolution software, and the log S-pH data are fitted to it by a weighted nonlinear regression procedure, where the following residual function was minimized, $$r = \sum_i^N \frac{(\log S_i^{obs} - \log S_i^{calc})^2}{\sigma_i^2(\log S)} \quad (25)$$

where N is the measured number of solubility values in the model, and log S$_i^{calc}$ is the calculated log solubility, which is a function of the refined parameters: pK$_a^{APP}$ (apparent ionization constant), log S$_o^{APP}$ (apparent intrinsic solubility), log S$_o$ (true intrinsic solubility—cases 1a and 1b in FIG. 8 only), log K$_n$ (aggregation constant), and n (aggregation order). The estimated standard deviation in the observed log S, σ$_i$, was estimated as 0.05 (log units). The overall quality of the refinement was assessed by the "goodness-of-fit,"

$$GOF = \sqrt{\frac{r}{N - N_p}} \quad (26)$$

where N$_p$ is the number of refined parameters.

In Table 3 all refined results of this example of solubility measurement are summarized. Underlying the refined values are about 1200 individual-pH solubility measurements, collected rapidly by the robotic instrument.

TABLE 3

| COMPOUND | pK$_a$ | EXCIPIENT | S$_o^{APP}$ ± SD | S$_o$ ± SD | log K$_n$ ± SD | type | n ± SD | pK$_a^{APP}$ ± SD | GOF | N |
|---|---|---|---|---|---|---|---|---|---|---|
| astemizole | 8.60 | none | 0.29 ± 0.08 | | 5.07 ± 0.44 | ⊕ | 1.8 | 8.9 ± 0.3 | 3.0 | 11 |
| | 5.84 | 0.1M KCl | 0.19 ± 0.03 | | 5.00 ± 0.21 | ⊕ | 2.4 | 9.2 ± 0.6 | 1.2 | 6 |
| | | 0.2M KCl | 0.27 ± 0.04 | | 4.39 ± 0.27 | ⊕ | 2.4 | 8.8 ± 0.4 | 1.4 | 6 |
| | | 0.24% PG | 0.22 ± 0.05 | | 3.17 ± 0.53 | ⊕ | 3.5 | 8.7 ± 0.2 | 2.3 | 6 |
| | | 1% PG | 0.22 ± 0.04 | | 3.27 ± 0.41 | ⊕ | 3.6 | 8.7 ± 0.4 | 1.8 | 6 |
| | | 5% PG | 0.31 ± 0.07 | | 4.66 ± 0.33 | ⊕ | 2.2 | 9.0 ± 0.5 | 1.8 | 6 |
| | | 0.24% NMP | 0.38 ± 0.06 | | 4.89 ± 0.24 | ⊕ | 2.2 | 9.1 ± 0.5 | 1.4 | 6 |
| | | 1% NMP | 0.38 ± 0.08 | | 5.67 ± 0.23 | ⊕ | 1.6 | 9.3 ± 0.4 | 1.4 | 6 |
| | | 0.24% PEG400 | 0.48 ± 0.01 | | 7.50 ± 0.01 | ⊕ | 1.2 | 10.6 ± 0.2 | 0.1 | 5 |
| | | 1% PEG400 | 0.29 | | 7.11 ± 0.07 | ⊕ | 1.5 | 10.0 ± 0.2 | 1.1 | 4 |
| | | 5% PEG400 | 0.29 | | 7.87 ± 0.02 | ⊕ | 1.1 | 10.8 | 0.4 | 4 |
| | | 3 mM NaTC | 0.63 ± 0.07 | 0.2 ± 0.1 | | ○ | | 8.1 ± 0.1 | 0.9 | 6 |
| | | 15 mM NaTC | 3.0 ± 0.7 | 1.4 ± 0.7 | | ○ | | 8.3 ± 0.2 | 1.6 | 6 |
| | | 0.24% HP-b-CD | 0.63 ± 0.06 | | 4.79 ± 0.37 | ⊕ | 1.8 | 8.7 ± 0.1 | 0.8 | 6 |
| | | 1% HP-b-CD | 12 ± 2 | 4.0 ± 2.9 | | ○ | | 8.1 ± 0.3 | 1.6 | 6 |
| butacaine | 10.09 | none | 40 ± 6 | 1.9 ± 0.7 | | ○ | | 8.8 ± 0.2 | 1.2 | 10 |
| | 2.05 | 0.1M KCl | 83 ± 17 | 1.3 ± 0.8 | | ○ | | 8.3 ± 0.3 | 1.4 | 5 |

TABLE 3-continued

| COMPOUND | pK$_a$ | EXCIPIENT | S$_o^{APP}$ ± SD | S$_o$ ± SD | log K$_n$ ± SD | type | n ± SD | pK$_a^{APP}$ ± SD | GOF | N |
|---|---|---|---|---|---|---|---|---|---|---|
| | | 0.2M KCl | 78 ± 2 | 2.5 ± 0.2 | | ⊙ | | 8.6 ± 0.1 | 0.1 | 4 |
| | | 0.24% PG | 51 ± 4 | 2.3 ± 0.5 | | ⊙ | | 8.8 ± 0.1 | 0.4 | 4 |
| | | 1% PG | 69 ± 5 | 0.9 ± 0.2 | | ⊙ | | 8.2 ± 0.1 | 0.5 | 5 |
| | | 5% PG | 66 ± 9 | 1.5 ± 0.5 | | ⊙ | | 8.5 ± 0.2 | 0.9 | 5 |
| | | 0.24% NMP | 47 ± 3 | 2.1 ± 0.5 | | ⊙ | | 8.8 ± 0.1 | 0.6 | 6 |
| | | 1% NMP | 71 ± 5 | 1.9 ± 0.5 | | ⊙ | | 8.5 ± 0.1 | 0.5 | 6 |
| | | 0.24% PEG400 | 151 | 3.6 | | ⊙ | | 8.5 | —b | 2 |
| | | 1% PEG400 | 107 ± 2 | 2.8 ± 0.4 | | ⊙ | | 8.5 ± 0.1 | 0.1 | 3 |
| | | 5% PEG400 | 107 | 2.8 | | ⊙ | | 8.5 | —b | 1 |
| | | 3 mM NaTC | 50 ± 10 | 3.1 ± 1.6 | | ⊙ | | 8.9 ± 0.2 | 1.1 | 4 |
| | | 15 mM NaTC | 96 ± 4 | 2.3 ± 0.4 | | ⊙ | | 8.5 ± 0.1 | 0.2 | 4 |
| | | 0.24% HP-b-CD | 79 ± 4 | 2.0 ± 0.3 | | ⊙ | | 8.5 ± 0.1 | 0.3 | 6 |
| | | 1% HP-b-CD | 141 ± 7 | 1.5 ± 0.4 | | ⊙ | | 8.1 ± 0.1 | 0.3 | 6 |
| clotrimazole | 6.02 | none | 0.39 ± 0.18 | | 5.93 ± 0.39 | ⊕ | 1.4 | 7.4 ± 1.1 | 2.8 | 11 |
| | | 0.1M KCl | 0.39 | | 6.20 ± 0.06 | ⊕ | 1.6 | 7.4 | 0.9 | 4 |
| | | 0.2M KCl | 4.8 ± 1.3 | 3.3 ± 1.2 | | ⊙ | | 5.9 ± 0.2 | 1.2 | 6 |
| | | 0.24% PG | 1.1 ± 0.2 | | 4.50 ± 0.22 | ⊕ | 1.6 | 6.5 ± 0.4 | 0.9 | 5 |
| | | 1% PG | 2.0 ± 0.5 | | 2.56 ± 0.73 | ⊕ | 2.3 | 6.1 ± 0.1 | 1.9 | 5 |
| | | 5% PG | 2.6 ± 1.0 | | 4.65 ± 0.53 | ⊕ | 1.4 | 6.3 ± 0.5 | 1.9 | 5 |
| | | 0.24% NMP | 1.3 ± 0.2 | | 4.59 ± 0.25 | ⊕ | 2.0 | 6.4 ± 0.3 | 1.3 | 6 |
| | | 1% NMP | 1.7 ± 0.2 | | 4.77 ± 0.16 | ⊕ | 1.8 | 6.5 ± 0.2 | 0.8 | 6 |
| | | 0.24% PEG400 | 0.39 | | 7.54 ± 0.03 | ⊕ | 1.3 | 7.9 | 0.6 | 4 |
| | | 1% PEG400 | 0.39 | | 7.15 | ⊕ | 1.9 | 7.4 | —b | 2 |
| | | 5% PEG400 | 1.9 ± 0.6 | | 6.86 ± 0.12 | ⊕ | 0.8 | 6.4 ± 0.1 | 0.1 | 4 |
| | | 3 mM NaTC | 1.0 ± 0.1 | | 5.23 ± 0.18 | ⊕ | 1.5 | 6.4 ± 0.2 | 0.9 | 5 |
| | | 15 mM NaTC | 20 ± 2 | 6.8 ± 1.4 | | ⊙ | | 5.5 ± 0.1 | 0.6 | 6 |
| | | 0.24% HP-b-CD | 17 ± 0.4 | 6.6 ± 0.4 | | ⊙ | | 5.6 ± 0.1 | 0.2 | 6 |
| | | 1% HP-b-CD | 85 ± 4 | 11.3 ± 2.0 | | ⊙ | | 5.1 | 0.4 | 6 |
| dipyridamole | 6.22 | none | 6.2 ± 1.1 | 2.3 ± 0.7 | | ⊙ | | 5.8 ± 0.1 | 2.1 | 6 |
| | | 0.1M KCl | 5.2 ± 0.8 | 3.3 ± 0.8 | | ⊙ | | 6.0 ± 0.1 | 0.8 | 6 |
| | | 0.2M KCl | 5.8 ± 0.9 | 3.1 ± 0.7 | | ⊙ | | 5.9 ± 0.1 | 0.8 | 6 |
| | | 0.24% PG | 5.8 ± 0.5 | 2.1 ± 0.3 | | ⊙ | | 5.8 ± 0.1 | 0.5 | 6 |
| | | 1% PG | 6.5 ± 0.3 | 2.7 ± 0.2 | | ⊙ | | 5.8 ± 0.1 | 0.3 | 6 |
| | | 5% PG | 9.8 ± 1.3 | 3.9 ± 0.8 | | ⊙ | | 5.8 ± 0.1 | 0.8 | 6 |
| | | 0.24% NMP | 5.9 ± 1.1 | 2.2 ± 0.6 | | ⊙ | | 5.8 ± 0.1 | 1.0 | 6 |
| | | 1% NMP | 8.1 ± 1.5 | 2.4 ± 0.7 | | ⊙ | | 5.7 ± 0.1 | 1.1 | 6 |
| | | 0.24% PEG400 | 4.6 ± 1.2 | | 6.95 ± 0.13 | ⊕ | 0.6 | 6.8 ± 0.1 | 0.4 | 4 |
| | | 1% PEG400 | 11 ± 3 | 5.0 ± 1.9 | | ⊙ | | 5.9 ± 0.2 | 1.3 | 6 |
| | | 5% PEG400 | 14 ± 1 | 13.7 ± 2.4 | | ⊙ | | 6.2 ± 0.1 | 0.4 | 4 |
| | | 3 mM NaTC | 24 ± 2 | 5.3 ± 0.9 | | ⊙ | | 5.6 ± 0.1 | 0.5 | 6 |
| | | 15 mM NaTC | 110 ± 5 | 9.9 ± 1.7 | | ⊙ | | 5.2 ± 0.1 | 0.4 | 6 |
| | | 0.24% HP-b-CD | 7.1 ± 0.8 | 2.8 ± 0.7 | | ⊙ | | 5.8 ± 0.1 | 0.8 | 6 |
| | | 1% HP-b-CD | 15 ± 1 | 3.2 ± 0.7 | | ⊙ | | 5.6 ± 0.1 | 0.6 | 6 |
| griseofulvin | | none | 14 ± 0.4 | | | | | | | 3 |
| | | 0.1M KCl | 21 ± 1 | | | | | | | 3 |
| | | 0.2M KCl | 19 ± 2 | | | | | | | 3 |
| | | 0.24% PG | 18 ± 2 | | | | | | | 3 |
| | | 1% PG | 24 ± 1 | | | | | | | 3 |
| | | 5% PG | 25 ± 2 | | | | | | | 3 |
| | | 0.24% NMP | 19 ± 1 | | | | | | | 3 |
| | | 1% NMP | 25 ± 1 | | | | | | | 3 |
| | | 0.24% PEG400 | 20 ± 2 | | | | | | | 3 |
| | | 1% PEG400 | 20 ± 1 | | | | | | | 3 |
| | | 5% PEG400 | 27 ± 2 | | | | | | | 3 |
| | | 3 mM NaTC | 39 ± 2 | | | | | | | 3 |
| | | 15 mM NaTC | 54 ± 2 | | | | | | | 3 |
| | | 0.24% HP-b-CD | 23 ± 2 | | | | | | | 3 |
| | | 1% HP-b-CD | 24 ± 1 | | | | | | | 3 |
| progesterone | | none | 17 ± 1 | | | | | | | 3 |
| | | 0.1M KCl | 23 ± 1 | | | | | | | 3 |
| | | 0.2M KCl | 20 ± 1 | | | | | | | 3 |
| | | 0.24% PG | 18 ± 3 | | | | | | | 3 |
| | | 1% PG | 19 ± 2 | | | | | | | 3 |
| | | 5% PG | 24 ± 14 | | | | | | | 3 |
| | | 0.24% NMP | 14 ± 2 | | | | | | | 3 |
| | | 1% NMP | 20 ± 1 | | | | | | | 3 |
| | | 0.24% PEG400 | 18 ± 1 | | | | | | | 3 |
| | | 1% PEG400 | 15 ± 2 | | | | | | | 3 |
| | | 5% PEG400 | 30 ± 6 | | | | | | | 3 |
| | | 3 mM NaTC | 22 ± 1 | | | | | | | 3 |
| | | 15 mM NaTC | 48 ± 3 | | | | | | | 3 |
| | | 0.24% HP-b-CD | 162 ± 9 | | | | | | | 2 |
| | | 1% HP-b-CD | 187 ± 6 | | | | | | | 3 |
| glybenclamide | 5.90 | none | 0.35 ± 0.10 | | 7.23 ± 0.16 | ⊖ | 1.1 ± 0.1 | 4.3 ± 0.1 | 1.4 | 11 |
| | | 0.1M KCl | 0.35 | | 6.97 ± 0.15 | ⊖ | 1.1 ± 0.2 | 4.3 | 2.7 | 6 |
| | | 0.2M KCl | 0.35 | | 6.99 ± 0.06 | ⊖ | 1.2 ± 0.1 | 4.3 | 1.1 | 5 |
| | | 0.24% PG | 0.35 | | 7.36 ± 0.12 | ⊖ | 1.1 ± 0.2 | 4.3 | 2.4 | 5 |
| | | 1% PG | 0.35 | | 7.34 ± 0.08 | ⊖ | 1.1 ± 0.1 | 4.3 | 1.7 | 5 |

TABLE 3-continued

| COMPOUND | pK$_a$ | EXCIPIENT | S$_o^{APP}$ ± SD | S$_o$ ± SD | log K$_n$ ± SD | type | n ± SD | pK$_a^{APP}$ ± SD | GOF | N |
|---|---|---|---|---|---|---|---|---|---|---|
| | | 5% PG | 0.71 | | 7.37 ± 0.02 | ⊖ | 1.0 ± 0.04 | 4.2 ± 0.2 | 0.5 | 6 |
| | | 0.24% NMP | 0.45 ± 0.11 | | 6.95 ± 0.15 | ⊖ | 1.0 | 4.6 ± 0.1 | 1.2 | 6 |
| | | 1% NMP | 0.65 ± 0.10 | | 6.92 ± 0.08 | ⊖ | 0.8 ± 0.1 | 4.7 ± 0.1 | 0.5 | 6 |
| | | 0.24% PEG400 | 0.36 | | 5.96 ± 0.09 | ⊖ | 0.9 ± 0.2 | 5.4 ± 0.1 | 0.6 | 5 |
| | | 1% PEG400 | 0.26 | | 6.88 ± 0.09 | ⊖ | 0.9 ± 0.1 | 4.7 ± 0.2 | 1.0 | 6 |
| | | 5% PEG400 | 2.69 | | 5.95 ± 0.36 | ⊖ | 0.8 ± 0.5 | 5.6 ± 0.2 | 1.0 | 6 |
| | | 3 mM NaTC | 0.32 | | 7.42 ± 0.03 | ⊖ | 1.2 ± 0.04 | 4.3 ± 0.1 | 0.4 | 6 |
| | | 15 mM NaTC | 2.5 ± 1.6 | | 6.69 ± 0.52 | ⊖ | 0.5 ± 0.2 | 5.5 ± 0.1 | 0.5 | 6 |
| | | 0.24% HP-b-CD | 4.4 ± 1.7 | | 6.67 ± 0.39 | ⊖ | 0.9 ± 0.2 | 5.1 ± 0.1 | 0.6 | 6 |
| | | 1% HP-b-CD | 24 ± 5 | | 6.79 ± 0.32 | ⊖ | 0.7 ± 0.1 | 5.4 ± 0.1 | 0.2 | 6 |
| mefenamic-acid | 4.54 | none | 0.021 ± 0.005 | | 6.02 ± 0.80 | ⊖ | 2.6 ± 2.1 | 4.3 ± 0.3 | 3.6 | 18 |
| | | 0.1M KCl | 0.023 ± 0.005 | | 6.61 ± 0.60 | ⊖ | 3.5 | 4.4 ± 0.4 | 2.0 | 5 |
| | | 0.2M KCl | 0.021 | | 5.72 ± 0.38 | ⊖ | 2.1 ± 1.1 | 4.3 | 3.7 | 3 |
| | | 0.24% PG | 0.021 | | 6.88 ± 0.54 | ⊖ | 3.3 ± 1.2 | 4.1 ± 0.3 | 1.4 | 3 |
| | | 1% PG | 0.021 | | 6.46 ± 0.72 | ⊖ | 2.0 ± 1.2 | 4.0 ± 0.3 | 4.2 | 3 |
| | | 5% PG | 0.056 | | 5.87 ± 0.09 | ⊖ | 0.9 ± 0.1 | 4.0 | 1.0 | 4 |
| | | 0.24% NMP | 0.019 ± 0.009 | | 6.22 ± 0.58 | ⊖ | 2.0 | 4.1 ± 0.6 | 3.4 | 6 |
| | | 1% NMP | 0.062 ± 0.010 | | 5.01 ± 0.55 | ⊖ | 2.5 ± 1.8 | 4.4 ± 0.2 | 1.3 | 6 |
| | | 0.24% PEG400 | 0.004 ± 0.002 | | 5.15 ± 1.08 | ⊖ | 2.5 | 4.5 ± 0.2 | 4.4 | 6 |
| | | 1% PEG400 | 0.021 | | | ⊖ | | 4.5 | 1.1 | 4 |
| | | 5% PEG400 | 0.028 | | 4.98 ± 0.58 | ⊖ | 0.6 | 4.5 ± 1.1 | 1.7 | 6 |
| | | 3 mM NaTC | 1.9 ± 0.4 | 0.11 ± 0.03 | | o | | 5.8 ± 0.1 | 0.4 | 3 |
| | | 15 mM NaTC | 1.4 ± 0.3 | 0.10 ± 0.03 | | o | | 5.7 ± 0.1 | 1.0 | 6 |
| | | 0.24% HP-b-CD | 0.34 ± 0.02 | 0.28 ± 0.02 | | o | | 4.6 ± 0.1 | 0.2 | 6 |
| | | 1% HP-b-CD | 2.9 ± 0.5 | 0.61 ± | | o | | 5.2 ± 0.1 | 1.1 | 6 |

Figure 9:
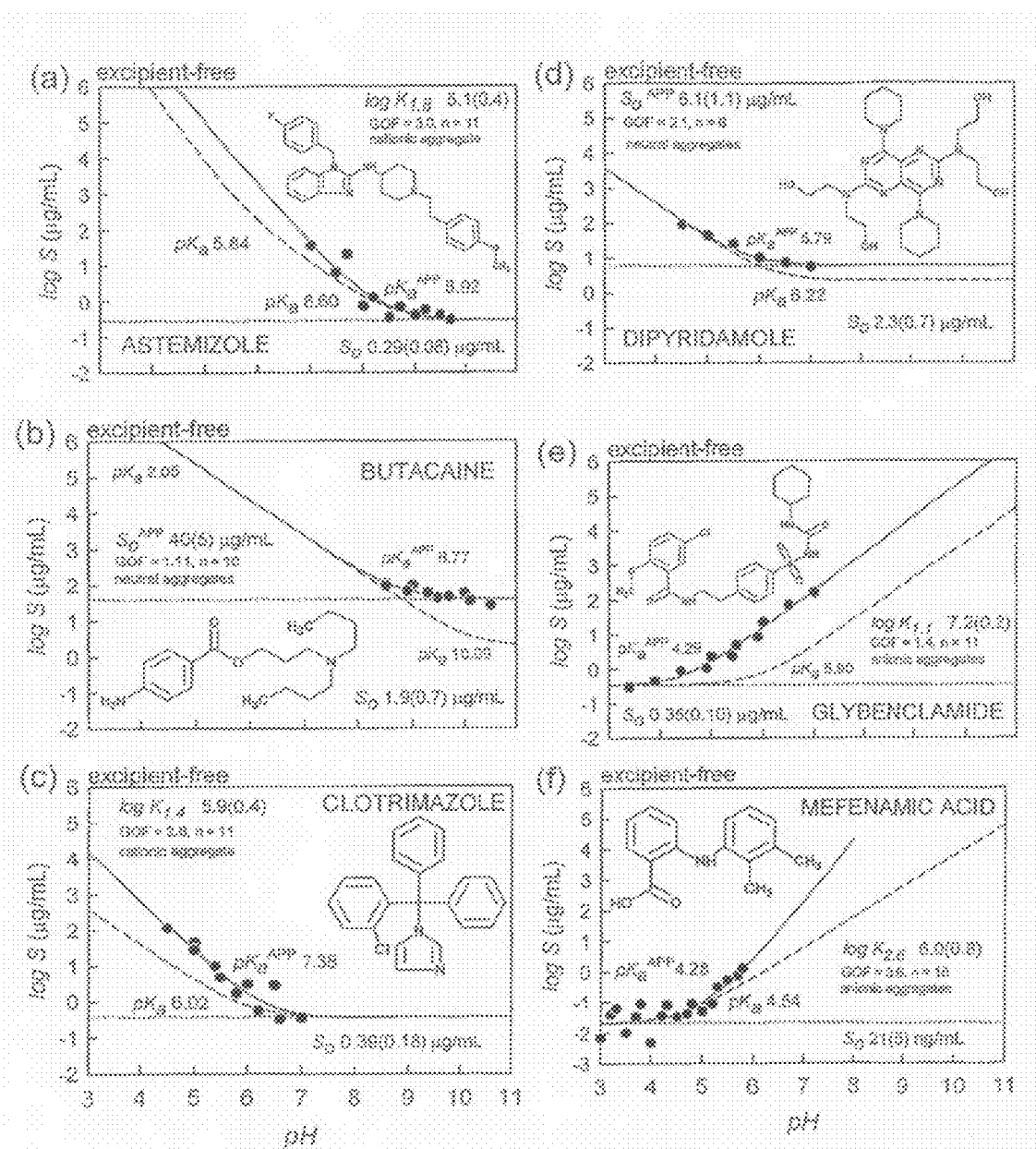
FIG. 9 shows excipient free log S vs. pH profiles for the compounds considered in the example of solubility measurements of the method from FIG. 1.

In FIG. 9 the log S-pH solubility plots are shown under excipient free conditions. The dashed curves correspond to those predicted by the Henderson-Hasselbalch equation (using the true pK$_a$), and are presented as a comparison to the curves more accurately representing the solubility-pH dependence. The dotted horizontal line indicates the apparent intrinsic solubility. The solid curve corresponds to the best fit of the actual data (filled circles). The bases studied here tended to form cationic aggregates (case 2b), with the exception of butacaine and dipyridamole, which apparently formed neutral aggregates (case 1b in FIG. 8). The two acids studied mostly form anionic aggregates (case 2a or case 3a in FIG. 8). It was not possible to apply the "pK$_a$-shift" method to the nonionizable compounds, so the degree to which aggregates may form is not known form this study.

Glybenclamide in FIG. 9e is an example of case 3a in the non-excipient results, since aggregates are suggested by the negative shift of 1.6 log units in the apparent pK$_a$, and the unit slope in the high-pH data. That is, the data are consistent with the formation of negatively-charged dimers, AH·A$^−$. Clotrimazole (FIG. 9c) appears to be composed of a combination of B·BH$^+$ and (BH$^+$)$_2$ species, as suggested by the slope value of n=1.4. Astemizole (FIG. 9a) appears to be composed of dimeric (n=1.8) (BH$^+$)$_2$ species, whereas mefenamic acid (FIG. 9f has both dimers and trimers of this type (n=2.6). Dipyridamole and butacaine represent case 1b behavior, where uncharged aggregates are hypothesized to form, which elevate the apparent solubility above the value expected if no aggregates formed, as that which would be expected from the HH equation (dash curves). These two molecules are also the most soluble of the ionizable molecules considered. As pointed out elsewhere (e.g. Avdeef A. et al., "Dissolution-Solubility: pH, Buffer, Salt, Dual-Solid, and Aggregation Effects", in: Testa, B. et al., "Comprehensive Medicinal Chemistry II", Vol. 5, ADME-TOX Approaches, Elsevier: Oxford, UK, 2006), it is not possible to assess the degree of aggregation (n) from the log S-pH data, when case 1a or case 1b dependence is indicated.

It is clear that all of the compounds discussed here are sparingly soluble in excipient free buffer ("none" row in Table 3), with mefenamic acid being the least soluble, at 21±5 ng/mL. It may be quite surprising that such a low value can be obtained by a high-throughput microtitre method. It might be even suggested that the 18-h incubation time used is anything but "high-throughput." But, it must be noted that during a 24-h duty cycle of the instrument, four to ten 96-well plates can be processed. It is this parallel nature of the robotic measurement which make the overall procedure very fast. The 18-h incubation time increases the probability that the measured results represent the true equilibrium solubility values of the most stable polymorph of the drug, and not the kinetic values of other fast methods, those based on the use of turbidity detection.

The intrinsic solubility of astemizole, clotrimazole, and glybenclamide are measured as 0.3-0.4 µg/mL (Table 3). The intrinsic solubility of dipyridamole was 6.2±1.1 µg/mL. The nonionizable compounds, griseofulvin and progesterone, are moderately soluble in comparison to the other compounds, measuring at 14-17 µg/mL. The most soluble compound studied is butacaine, with intrinsic solubility of 40±6 µg/mL. It is clear from these and other measurements (below) that the sensitivity of the µSOL Evolution method reaches the low nanogram region, in part made possible by the highly-developed spectroscopic data processing software in the Evolution instrument.

Figures corresponding to FIG. 9 and showing some of the log S-pH curves for the ionizable molecules studied, at one of the excipient concentrations (1%, 15 mM, or 0.2 M) can be provided as well. The results of the other excipient concentrations considered are summarized in Table 2. In addition to the curves in the excipient free plots (FIG. 9), such figures have an additional "dash-dot-dot" curves, which represent the solid curves from the excipient-free case. This baseline curve allows for quick visual assessment of the impact of the excipient on a particular compound.

With respect to potassium chloride, the general patterns are similar to those in the excipient-free cases (FIG. 9). The apparent intrinsic solubility of only butacaine and clotrimazole are significantly elevated by 0.2 M KCl. Astemizole seems to show a steeper pH dependence in neutral pH solutions, putatively arising from the formation of higher-order aggregates. Clotrimazole seems to show the opposite effect:

the presence of high-salt concentration seems to break up the aggregates seen in excipient-free solution. Its behavior in 0.2 M KCl is well predicted by the Henderson-Hasselbalch equation. Also, its intrinsic solubility lifts from 0.39 to 3.3 µg/mL. The effect of 0.2 M KCl on dipyridamole, glybenclamide, and mefenamic acid appear minimal. The deflection of points from the curve for pH>6.5 for mefenamic acid could be due to salt formation.

With respect to Propylene Glycol, the effects are similar to those due to 0.2 M KCl (FIG. 3). Astemizole appears to show even higher-order aggregates (n=3.6), along with a slight decrease in intrinsic solubility. The solubility appears to increase only in low-pH solutions for astemizole. The intrinsic solubility of clotrimazole increases from 0.39 to 2.0 µg/mL.

With respect to 1-Methyl-2-Pyrrolidone, the aggregation order diminishes in astemizole and glybenclamide, compared to the two previous excipients discussed. The other effects are comparatively smaller in degree. Clotrimazole appears to be enhanced in solubility with NMP, as with KCl and PG. Mefenamic acid responds to NMP with a slight increase in intrinsic solubility.

With respect to Propylene Glycol 400, whereas the first three excipients discussed are associated with weak effects, PEG400 has a moderate impact. The binding constant of aggregation in astemizole and clotrimazole (but not the order of aggregation) greatly increase, as indicated by dramatic shifts of the solid curves to higher pH values. The aggregation in mefenamic acid appears to disappear, and the curve has classic HH behavior. The apparent intrinsic solubility of the more soluble drugs, dipyridamole and butacaine, nearly double over values shown in the previous three weaker-acting excipients.

With respect to Sodium Taurocholate, the patterns of effect for each of the considered drugs is dramatic, with an across-the-board elevation of solubility, particularly in the case of mefenamic acid (Table 2). Astemizole behaves as a classical HH-obeying molecule, as do all the other molecules, except glybenclamide. The latter molecule shows pH dependency of +0.5, which may be best described by Case $3ax$ behavior. Unfortunately, not enough data were collected in alkaline pH to further test the aggregation model. Most of the aggregation-prone molecules are strongly bound to NaTC micelles, apparently as uncharged monomers, whose pH dependence can be described by the HH equation. The analysis of the apparent binding strength can be described by case $1a$ or $1b$ equations.

With respect to 2-Hydroxypropyl-β-Cyclodextrin, as with the bile salt, 1% HP-β-CD, has the tendency to bust up aggregates. Although the solubility reactions is represented by an aggregation model, the association is that of complexation. The aggregation model is still convenient in categorizing the solubility effects, in order to compare this to the action of the other excipients with a similar model. Both the bile salt and the cyclodextrin have a significant effect on elevating solubility of the drugs studied. Both excipients appear to diminish the formation of aggregates. Glybenclamide still has the unique half-pH slope in the solubility-pH plot.

With respect to Astemizole, Table 2 is a convenient reference in comparing the effects of all the excipients on a particular drug. In the case of astemizole, solubility is greatly enhanced by 1% HP-β-CD (excipient-free value of 0.29 µg/mL raised to 12 µg/mL) and also by 15 mM NaTC. The strength of aggregation (log $K_n/n$) is elevated most significantly by 0.24% and 5% PEG400, over values in excipient-free solutions. Slightly lesser elevations are noted with 1% PEG400 and 1% NMP.

With respect to Butacaine, it is to state that Butacaine does not appear to form charged aggregates. The solubility of the most soluble molecule of those considered here, is most easily elevated by not only both of the HP-β-CD concentrations (Table 2), but also by 0.1 M KCl, all PEG400 concentrations (excipient-free value of 40 µg/mL raised to 152 µg/mL), and 15 mM NaTC.

With respect to Clotrimazole, as with astemizole, the aggregates with clotrimazole are widely affected by various excipients. The strength of aggregation (log $K_n/n$) is significantly elevated by 0.24% and 5% PEG400. The biggest gains in solubility come from the use of 15 mM NaTC and 1% HP-β-CD (excipient-free value of 0.39 µg/mL raised to 85 µg/mL).

With respect to Dipyridamole, the PEG400 aggregation strengthening effect is seen with dipyridamole at the low excipient concentration. Solubility is elevated to 110 µg/mL from the excipient-free value of 6.2 µg/mL by 15 mM NaTC. Other excipients have significant effects on solubility (Table 2).

With respect to Griseofulvin, aggregation phenomena cannot be indicated by the "$pK_a$-shift" method, since both griseofulvin and progesterone are nonionizable. The elevation of solubility takes place with the "strong" excipients: excipient-free value of 14 µg/mL raised to 54 µg/mL by 15 mM NaTC. The impact of the excipients on the solubility of griseofulvin is relatively less dramatic than that on other lesser soluble drugs studied.

With respect to Progesterone, in contrast to griseofulvin, progesterone is strongly affected by cyclodextrin. As with griseofulvin, the elevation of solubility takes place with the "strong" excipients: but the excipient-free value of 17 µg/mL is raised to 187 µg/mL by 1% HP-β-CD with progesterone.

With respect to Glybenclamide, the strength of aggregation with glybenclamide is only increased by the excipients, especially 15 mM NaTC. This may be a "salting-out" phenomenon, appearing most often with PEG400. This is a new and unexpected observation, and will require further investigation.

With respect to Mefenamic Acid being by far the least soluble drug of the set measured, the best enhancement to solubility is effected by NaTC and HP-β-CD, but the highest intrinsic solubility achieved is still relatively low, less than 3 µg/mL. NMP and PEG seem to increase the aggregation strength (log $K_n/n$).

Summarizing the above described results of this example of solubility measurement, it should not be a mystery that excipients raise the solubility of sparingly soluble molecules, as illustrated. Perhaps what is not well known is that the extent and nature of such effects can be very quickly and reliably assessed by the robotic instrument used. By comparisons of the results to those derived from DMSO-free shake-flask methods, the values appear acceptably accurate, in spite of the presence of 1% DMSO in all of the solutions in this study. Considering the effects of specific excipients, perhaps the new observation is that PEG400 (and to a lesser extent, NMP) seems to increase the strength of aggregation (log $K_n/n$) of a number of the drugs. The nature of the interactions are not entirely understood, but perhaps it is useful to consider the following possible effect. The moderate strength PEG400 may not provide a sufficiently competitive hydrophobic environment into which to attract the drugs, compared to that of cyclodextrin and sodium taurocholate. However, the 1% DMSO present in all solutions and some water of solvation may be attracted to the PEG400 molecules, making the excipient-poor portion of the buffer solution more concentrated in the drug aggregates, leading to their stronger self-associations. Of course, the analogy of the "salting out" effect is used.

Figure 10:
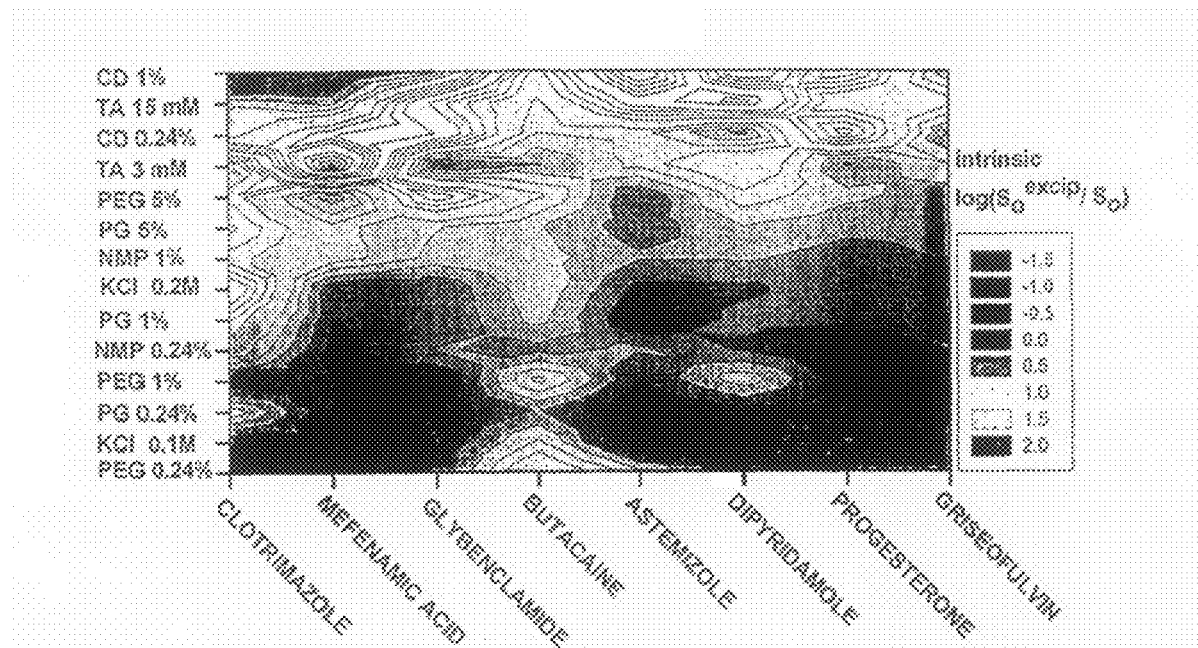
FIG. 10 shows a rank-ordered Solubility Excipient Classification Gradient Map for the compounds and excipient combinations of the example of solubility measurements of the method from FIG. 1.

As correspondingly shown for results of the exemplary permeability measurements above, a mapping scheme is shown in FIG. 10, called S-Mapping, which improves the visual aspects of the excipient effects on solubility, allowing for precise systematic evaluation. The map can be automatically generated by software associated with the solubility instrument used in this measurement of solubility. Plotted in FIG. 10 are apparent intrinsic log solubility ratios, with excipient solubility divided by excipient-free base value. Such a "gradient" map normalizes solubility to shift patterns with reference to the excipient-free baseline. Since 1% DMSO is present in all solutions, a gradient map is expected to eliminate some of the impact of DMSO. In FIG. 10, green values represent the base (unaffected) values. Warm colors (yellow to deep orange) represent enhanced solubility, and cool colors (deep blue) refer to depressed values. Along the vertical axes are the excipient compositions, rank ordered by decreasing average intrinsic solubility enhancement. Along the horizontal axes are the drugs, arranged in the order decreasing benefit due to excipients. The top left corner represents the "best" combination of excipients and compounds. The lower right corner represents the "worst" combination. With this Solubility-Excipient Classification Gradient Map, or S-Mapping for short, it would be very efficient to recognize and thus prioritize the most promising molecule-excipient combinations, and such S-Mapping schemes can be rapidly developed for very large numbers of molecules, as are encountered in discovery-optimization programs in pharmaceutical companies.

The three most helpful excipients in this example of solubility measurement appear to be 1% HP-β-CD, 15 mM NaTC, and 0.24% HP-β-CD. The least-effective excipients are 0.24% PEG400, 0.1M KCl, and 0.24% PG. From FIG. 10, it is visually apparent that clotrimazole, with its relatively "warm" colored vertical track in the map, is ranked high overall. Not only is solubility enhanced by the strong excipients, such as 1% HP-β-CD, it is also elevated by moderate and relatively weak excipients, such as 0.2 M KCl. As S-Mapping visually indicates, the solubility enhancement of progesterone and griseofulvin is weak and comparable, and these two molecules are classed to the right side of the map. Only at the top of the map does progesterone shows some warm color effects, differentiating itself slightly from griseofulvin.

In the step of combining the permeability measurement results and the solubility measurement results into the flux function of the first embodiment of the method according to the invention, it is proposed to logically combine PAMPA-excipient measurements as described above and solubility-excipient measurements as described above into a pH dependent flux function, graphically represented by the novel, rank-ordered, Biopharmaceutics Classification Gradient Map. Therein, eight sparingly soluble drugs (astemizole, butacaine, clotrimazole, dipyridamole, griseofulvin, progesterone, glybenclamide, and mefenemic acid) are used, being measured in fifteen combinations of six excipients (sodium taurocholate, 2-hydroxypropyl-β-cyclodextrin, potassium chloride, propylene glycol, 1-methyl-2-pyrrolidone, and polyethylene glycol 400) as a basis to illustrate the screening methodology according to the invention. Three additional molecules (albendazole, amiodarone, and naproxen) are similarly characterized with 2-hydroxypropyl-β-cyclodextrin (HP-β-CD). Some of the HP-β-CD results are compared with available in vivo data. Moreover, it is shown that the classical Brodie pH Partition Hypothesis, now widely accepted in pharmaceutical research, can break down when low-solubility and high-permeability drugs are considered, where the pH effect is actually inverted (i.e., the pH where the drug is more charged showing higher absorptive flux than the pH where the drug is more neutral). This phenomenon is referred to as the pH Partition Antithesis effect.

As basis for said step of combining the permeability measurement results and the solubility measurement results into the flux function, with respect to solubility and permeability in Fick's first law, it is to state that under steady-state (i.e., linear spatial concentration gradient of the permeant in the membrane) sink condition (i.e., zero permeant concentration on the acceptor side of the membrane barrier), Fick's first law applied to homogeneous membranes may be stated as $$J = D_m PC^{APP} C_D / h \quad (27)$$
$$= P_e C_d$$

where J is the flux (mol cm$^{-2}$ s$^{-1}$) of the permeant molecule, $D_m$ is the permeant diffusivity (cm$^2$ s$^{-1}$) in the membrane phase, $PC^{APP}$ is the apparent (pH-dependent) partition coefficient of the permeant between aqueous solution and the membrane, $C_D$ (mol cm$^{-3}$) is the concentration of the permeant molecule on the donor side of the membrane, h (cm) is the thickness of the membrane, and $P_e$ (cm s$^{-1}$) is the "effective" permeability, a product of three transport parameters in eq. (3). $C_D$ is equal to the dose of the drug, unless the dose exceeds the solubility limit, in which case it's equal to the solubility (a "saturated" solution). If effects such as the aqueous boundary layer (ABL) resistance, the formation of aggregates, and other such complications, are neglected the HH equation applied to a saturated solution produces $$\log J_{satd} = \log P_e + \log S \quad (28)$$
$$= \log[P_o / (10 \pm (pH - pKa) + 1)] +$$
$$\log[S_o(10 \pm (pH - pKa) + 1)]$$
$$= \log P_o + \log S_o$$

with '+' used for acids, and '−' used for bases. $P_o$ and $S_o$ are the pH-independent intrinsic permeability and solubility, respectively. The concentration of the drug, $C_D$, is less than or equal to the solubility, S. Likewise, the concentration of the uncharged species, $C_o$, is always equal to or less than the intrinsic solubility of the species, $S_o$. According to equation (28), flux in a saturated solution is pH-independent. It thus stands to reason that the pH Partition Hypothesis does not hold in a saturated solution. However, as show below, flux in a saturated solution can have pH dependence, but not necessarily the one predicted by the pH Partition Hypothesis.

Figure 11:
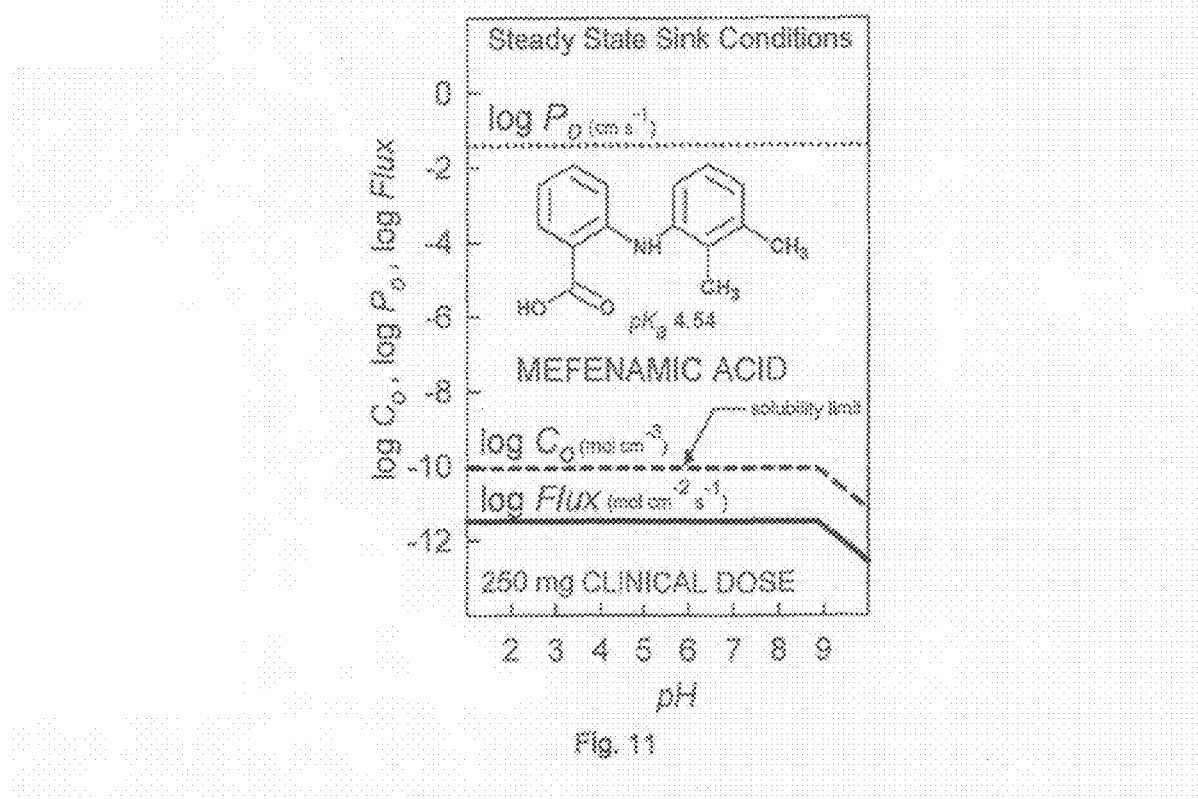
FIG. 11 shows plots of log $P_o$, log $C_o$, and log $P_oC_o$ (flux) vs. pH for mefenamic acid, at the clinical dose of 250 mg, illustrating Fick's law based on intrinsic concentrations in the method from FIG. 1.

FIG. 11 illustrates this flux relationship for mefenamic acid, a sparingly-soluble drug, using literature values for intrinsic permeability and solubility, assuming that the ideal Henderson-Hasselbalch equation holds (i.e., no solute dimers or trimers form, no ABL resistance is encountered, membrane retention is absent, etc.). The intrinsic permeability does not depend on pH (dotted line in FIG. 11), but its cofactor in the flux equation, $C_o$, does (dashed line). In solutions that are saturated in part (pH<9 at 250 mg clinical dose), the plot of log $C_o$ versus pH for an ionizable molecule is simply a combination of straight segments, joined at a point of discontinuity indicating the boundary between the saturated state and the state of complete dissolution. The pH of this junction point is dependent on the dose level used in the calculation, and the maximum value of $C_o$ is equal to $S_o$ in a saturated solution (equation (28)).

FIG. 11 shows that log $C_o$ (dashed line) is a horizontal line in the saturated solution (log $C_o$=log $S_o$), and decreases with a slope of −1 in the pH domain where the solute is completely dissolved. At the clinical dose level, the calculated inflection is at pH 9, and at lower doses, the point is at lower pH (e.g., for a 1 mg dose, the critical pH drops to 6.5). Only for doses below 5.3 μg/250 mL for mefenamic acid, is the log $C_o$ curve entirely below the dose-solubility limit, taking on a hyperbolic shape. The log flux-pH curve is indicated by the solid line in FIG. 11, and is the summation of the log $P_o$ and log $C_o$ curves. It should be noted that the pH Partition Hypothesis holds across the entire pH range only in the case where dose<5.3 μg, since no solid forms. The pH Partition Hypothesis is valid at higher dose levels, but only above the pH where the solid entirely dissolves, in the regions defined by the diagonal solid lines (pH>9 for 250 mg dose).

With respect to conversion of intrinsic data to intestinal pH 5.0, pH 6.2, and pH 7.4 conditions constants were used to convert the above described permeability measurement results and the above described solubility measurement results to the intestinally relevant conditions of using equations more complex than that of Henderson-Hasselbalch. Referring to solubility, six different cases of aggregation-induced distortions of log S-pH curves have been described above. Two more equations are derived, and all of the solubility equations are summarized in Table 1. These equations are used to calculate S at pH 5.0, 6.2, and 7.4.

Referring to permeability, the pH dependence of the effective permeability is described by $$\frac{1}{P_e} = \frac{1}{P_{ABL}} + \frac{10^{\pm(pH-pK_o)}+1}{P_o} \quad (29)$$

(with '+' used for acids, and '−' used for bases), where $P_{ABL}$ is the aqueous boundary layer permeability. For an ABL thickness of h, (approximately 40 μm in the intestine), the ABL permeability may be estimated from $$P_{ABL} = D_{aq}/h \quad (30)$$

where $D_{aq}$ is the diffusivity of the drug in solution (cm² s⁻¹), which can be approximated at 25° C. by the molecular weight-based formula, log $D_{aq}$=−4.15−0.448 log MW (Avdeef A. et al. "Permeability of Weakly Basic Drugs Predicted with the Double-Sink PAMPA $pK_a^{flux}$ Method. Layer", Eur. J. Pharm. Sci., 2005, 24, 333-349). Equation (29) and equation (30) are used to convert the intrinsic permeability into the effective values at pH 5.0, 6.2, and 7.4, assuming h=40 μm.

In Table 2 the refined results from this example of combining the permeability measurement results and the solubility measurement results into the flux function are summarized, with and without 1% HP-β-CD. The rest of the data used is taken from the example of permeability measurements described above and the example of solubility measurements

TABLE 4

| CASE | AGGREGATION REACTIONS | SOLUBILITY EQUATIONS |
|---|---|---|
| 1A | n HA ⇌ (HA)$_n$ | log S = log $S_o$ + log (1 + $K_a$/[H⁺] + n $K_n$⊙$S_o^{n-1}$) |
| 1B | n B ⇌ (B)$_n$ | log S = log $S_o$ + log (1 + [H]⁺/$K_a$ + n $K_n$⊙$S_o^{n-1}$) |
| 2A | n A⁻ ⇌ (A⁻)$_n$ | log S = log $S_o$ + log (1 + $K_a$/[H⁺] + n $K_n^\ominus K_a^n S_o^{n-1}$/[H⁺]$^n$) |
| 2B | n BH⁺ ⇌ (BH⁺)$_n$ | log S = log $S_o$ + log (1 + [H⁺]/$K_a$ + n $K_n^\oplus$[H⁺]$^n S_o^{n-1}/K_a^n$) |
| 3A | n A⁻ + n HA ⇌ (AH•A⁻)$_n$ | log S = log $S_o$ + log (1 + $K_a$/[H⁺] + 2n $K_n^* K_a^n S_o^{2n-1}$/[H⁺]$^n$) |
| 3B | n BH⁺ + n B ⇌ (BH⁺•B)$_n$ | log S = log $S_o$ + log (1 + [H⁺]/$K_a$ + 2n $K_n^*$ [H⁺]$^n S_o^{2n-1}/K_a^n$) |
| 3AX | n A⁻ + n HA ⇌ (AH•A⁻)$_n$ & HA + X ⇌ HA•X | log S = log $S_o$ + log (1 + $K_a$/[H⁺] + 2n $K_n^* K_a^n S_o^{2n-1}$/[H⁺]$^n$ + K■) |
| 3BX | n BH⁺ + n B ⇌ (BH⁺•B)$_n$ & B + X ⇌ B•X | log S = log $S_o$ + log (1 + [H⁺]/$K_a$ + 2n $K_n^*$ [H⁺]$^n S_o^{2n-1}/K_a^n$ + K■) | described above. Underlying the refined intrinsic values are more than 2400 individual-pH solubility and permeability measurements. The examples in Table 5 show that cyclodextrin lowers permeability and raises solubility, but the two effects are not equal in magnitude.

TABLE 5

| COMPOUND | $pK_a$ | $P_e$(pH 5.0) (cm s⁻¹) | $P_e$(pH 6.2) (cm s⁻¹) | $P_e$(pH 7.4) (cm s⁻¹) | $P_o$ (cm s⁻¹) | GOF | N |
|---|---|---|---|---|---|---|---|
| albendazole (buffer) | 4.21, 10.43 | 292 | 328 | 330 | 4.28 ± 1.59 E−04 | 3.9 | 6 |
| (buffer + 1% w/v HP-b-CD) | | 30 | 31 | 31 | 3.12 ± 0.30 E−05 | 0.7 | 6 |
| amiodarone (buffer)[b] | 9.06 | 581 | 1110 | 1180 | 13 ± 3 | 2.1 | 9 |
| (buffer + 1% w/v HP-b-CD) | | 120 | 153 | 156 | 5.9 ± 1.7 | 2.8 | 6 |
| naproxen (buffer)[c] | 4.32 | 525 | 58 | 4 | 4.59 ± 0.58 E−03 | 1.8 | 24 |
| (buffer + 1% w/v HP-b-CD) | | 68 | 26 | 2 | 3.02 ± 0.35 E−03 | 1.1 | 5 |

| | | S(pH 5.0) (μg mL⁻¹) | S(pH 6.2) (μg mL⁻¹) | S(pH 7.4) (μg mL⁻¹) | $S_o^{APP}$ (μg mL⁻¹) | | |
|---|---|---|---|---|---|---|---|
| albendazole (buffer) | | 1.0 | 0.89 | 0.88 | 0.88 ± 0.07 | 0.7 | 5 |
| (buffer + 1% w/v HP-b-CD) | | 34 | 34 | 34 | 34 ± 1 | 0.3 | 12 |

TABLE 5-continued

| COMPOUND | pK$_a$ | P$_e$(pH 5.0) (cm s$^{-1}$) | P$_e$(pH 6.2) (cm s$^{-1}$) | P$_e$(pH 7.4) (cm s$^{-1}$)) | P$_o$ (cm s$^{-1}$) | GOF | N |
|---|---|---|---|---|---|---|---|
| amiodarone (buffer) | | 27 | 1.7 | 0.11 | 0.002 ± 0.002 | 3.1 | 4 |
| (buffer + 1% w/v HP-b-CD) | | 4188* | 245* | 14.7 | 0.18 ± 0.08 | 3.8 | 23 |
| naproxen (buffer) | | 101 | 1337 | 20893* | 18 ± 1 | 0.8 | 4 |
| (buffer + 1% w/v HP-b-CD) | | 182 | 206 | 585 | 180 ± 3 | 0.5 | 19 |

Regarding excipient gradients in permeability measurements at pH 5.0, pH 6.2, and pH 7.4, for all of the combinations of drugs and excipients are calculated from the intrinsic values described, using equation (29), with an ABL permeability corresponding to a layer of approximately 40 μm thickness factored in, using equation (30). A baseline permeability value was defined to be at pH 6.2, under 40 μm ABL thickness, and excipient-free (X=0) condition: $P_{e,6.2,40}^{X=0}$. All of the other values of permeability were divided by the base value, to obtain the ratios ($P_{e,pH,40}^{X}/P_{e,6.2,40}^{X=0}$). When a particular excipient or pH enhances permeability, the calculated ratio is greater than one. When the excipient/pH combination depresses permeability, then the calculated factor is less than one.

Figure 12A:
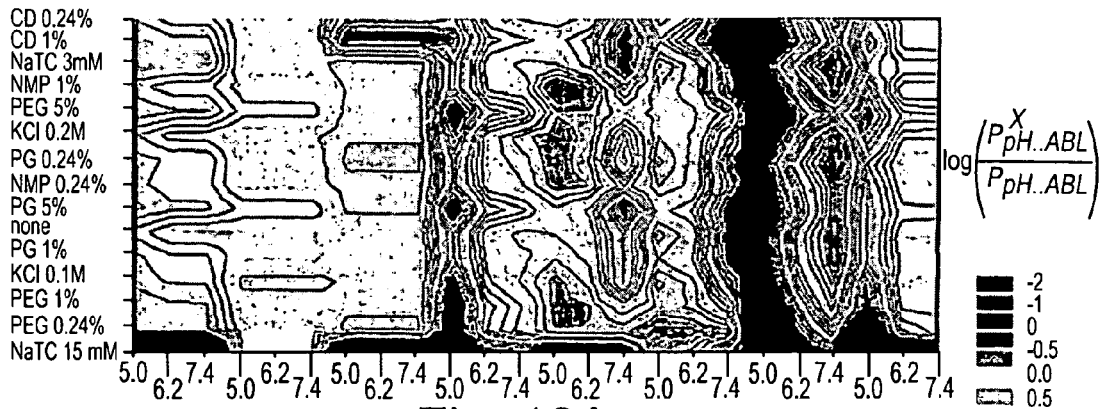
FIG. 12 shows: (a) PAMPA-Excipient-pH Classification Gradient Map of the in the method from FIG. 1; (b) Solubility-Excipient-pH Classification Gradient Map in the method from FIG. 1; and (c) Rank-ordered Biopharmaceutics Classification Gradient Map for the compounds and excipient combinations of the method from FIG. 1.

The PAMPA-Excipient-pH Classification Gradient Map, shown in FIG. 12a, is a rank-ordered contour plot of log($P_{e,pH,40}^{X}/P_{e,6.2,40}^{X=0}$) values. There are 360 gradients plotted in FIG. 2a. The above-zero gradients indicate permeability enhancement, and are represented by warm colors (orange, red). The below-zero gradients in the map indicate excipient/pH-depressed permeability, and is represented by cold colors (dark green, deep blue). In this map, yellow indicates the baseline level, where the gradients are nil. The plot is ranked-ordered based on flux gradients, described below.

From the PAMPA-Excipient-pH Classification Gradient Map in FIG. 12a, certain trends can be very quickly recognized. The "cold" deep-blue regions (depressed permeability) are mostly associated with 15 mM NaTC, pH 5 butacaine and dipyridamole, for most excipients. The "hot" zones (enhanced permeability) are with low-pH solutions for the two acids, glybenclamide and mefenamic acid, and for pH 7.4 butacaine. Also, progesterone, griseofulvin, and pH 7.4 astemizole are "warm" to a number of excipients.

Regarding gradients in micro solubility measurements at pH 5.0, pH 6.2, and pH 7.4, all of the combinations of drugs and excipients are calculated from the intrinsic solubility and aggregation constants, using the equations in Table 4. A baseline value solubility was defined to be at pH 6.2, under excipient-free (X=0) condition: $S_{6.2}^{X=0}$. All of the other values of solubility are divided by the base value, to obtain the ratios ($S_{pH}^{X}/S_{6.2}^{X=0}$). When a particular excipient or pH other than 6.2 enhances solubility, the calculated ratio is greater than one. When the excipient/pH combination depresses solubility, then the calculated factor is less than one.

Figure 12B:
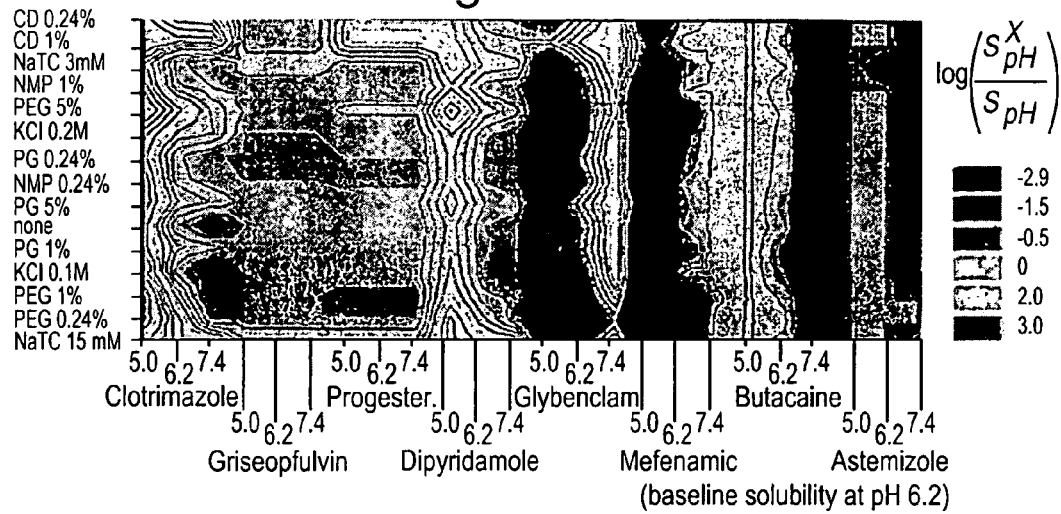

The Solubility-Excipient-pH Classification Gradient Map, shown in FIG. 12b, is a rank-ordered contour plot of log ($S_{pH}^{X}/S_{6.2}^{X=0}$) values. There are 360 gradients plotted in FIG. 12b. The above-zero gradients indicate solubility enhancement, and are represented by warm colors (orange, red). The below-zero gradients in the map indicate excipient/pH-depressed solubility, and is represented by cold colors (dark green, deep blue). In this map, light green indicates the baseline level, where the gradients are near zero. The plot is ranked-ordered based on flux gradients, described below.

From the Solubility-Excipient-pH Classification Gradient Map in FIG. 12b, certain trends can be very quickly recognized. The "cold" deep-blue bands (depressed solubility) are mostly associated low-pH glybenclamide and mefenamic acid, and with pH 7.4 butacaine and astemizole. The "hot" zones (enhanced solubility) are with low-pH clotrimazole and dipyridamole, and pH 7.4 glybenclamide solutions. Griseofulvin, progesterone, pH 7.4 mefenamic acid, pH 5 butacaine and astemizole all show excipient unperturbed solubility values. Since 1% DMSO is present in all solutions, a gradient map is expected to eliminate some of the impact of DMSO.

Further, salt effects are considered wherein the drugs selected have very low intrinsic solubility values, with mefenamic acid indicating 21 ng/mL intrinsic value. However, if the pK$_a$ of a molecule is far from the physiological range of 5-7.4, the pH-dependence described by the equations in Table 4 can elevate solubility to high values in the neutral-pH region (e.g., amiodarone and naproxen, Table 5). The formation of charged aggregates makes the pH dependence even steeper. With the appearance of charged species, solubility rises, but not indefinitely. At some high apparent solubility value, the solubility product of a salt formed between the charged drug and one of the counterions present in solution will be exceeded, and a salt-form of the charged drug will precipitate. The highest concentrations used (100-200 μM) are generally below the level of salt precipitation, with the exception of mefenamic acid at pH>7, as noted above. The reasonable assumption is made that the onset of salt precipitation is three orders of magnitude above the intrinsic solubility value found in the excipient-free case. This had been referred to as the "sdiff 3-4" approximation (Avdeef A., "Absorption and Drug Development—Permeability, Solubility, Charge State, Wiley-Interscience, 2003, pp. 116-246). The working premise is that even though this is an uncertain approximation, it is still better to take advantage of it than to completely ignore salt formation, which would attenuate solubility.

For example, the intrinsic solubility of naproxen was measured as 18 μg/mL in this study. According to the "sdiff 34" approximation, one should expect to see the formation of salt precipitate in high-pH solutions, if the calculated solubility (equations in Table 1) were to exceed 18 mg/mL. Using the HH equation, the calculated value of excipient-free solubility at pH 7.4 is 20.9 mg/mL. In Table 2, the naproxen pH 7.4 value is marked with an asterisk, to indicate that the anticipated 18 mg/mL salt limit is exceeded.

Using this "sdiff 3-4" approximation, the salt limits for the ionizable drugs in this study are 288 μg/mL for astemizole, 39.8 mg/mL for butacaine, 389 μg/mL for clotrimazole, 347 μg/mL for glybenclamide, and 21 μg/mL for mefenamic acid. With these limits, astemizole was predicted to have salt precipitation at pH 5 and 6.2, for all excipients, and at pH 7.4 for PEG400. Butacaine at pH 5 was expected to have salt precipitation. Clotrimazole at pH 5 with 0.24 and 1.0% PEG400 was expected to salt out. Glybenclamide and mefenamic acid at pH 7.4 were expected to salt out for several of the excipients. Also, mefenamic acid at pH 6.2 in 0.1 M KCl and 1% HP-β-CD is expected to precipitate as salts.

The salt limits were incorporated into the Solubility-Excipient-pH Classification Gradient Map in FIG. 12b.

Figure 12C:
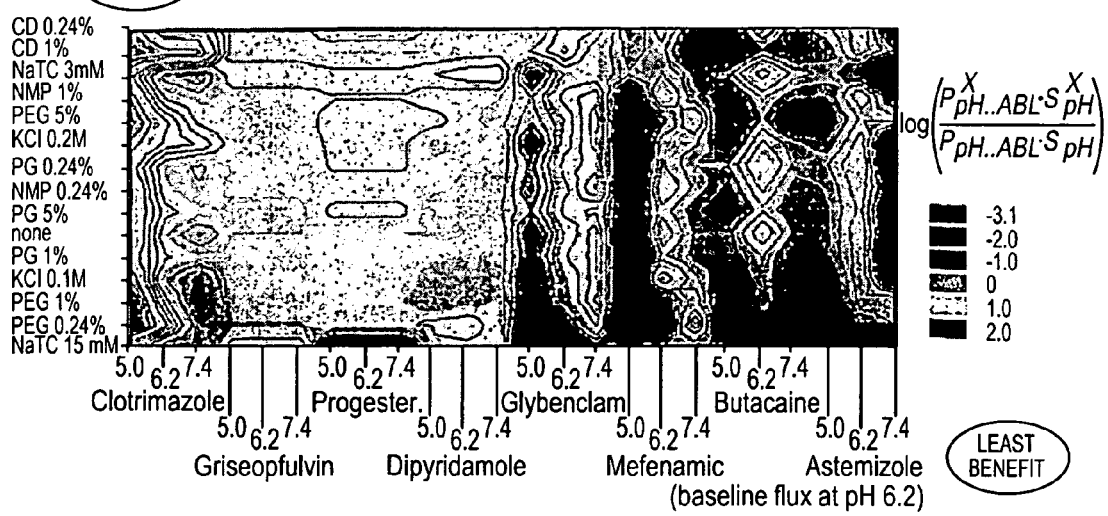

As can be seen in FIGS. 12a and 12b, the preceding two classification maps are largely opposites of one another. The regions in warm colors in one are matched by regions of cool colors in the other. Broadly, this is to be expected, since the pH dependence of permeability and solubility are inversely related, according to the simple HH equation (equation (28)). In the saturated solution portions of FIG. 11 (pH<9), using the simplistic HH equation, flux is pH-independent, since gains in one property are entirely offset by the losses in the other. It is not enough to use one or the other property to optimize on drug absorption, which is a flux-related property. Permeability and solubility, when combined, can serve optimization needs, yet this is seldom done in day-to-day practice in the pharmaceutical industry. Permeability (cellular) measurement is often done by biologists. Solubility measurement is often done by physical chemists. The two groups often are located in different buildings, and the two measurements are sometimes done at very different times. The coherent integration of the two sets of measurements is sometimes a daunting task. Early efforts to draw attention to the logical union of the two properties resulted in the AP (Dressman J. B. et al., "Absorption potential: estimating the fraction absorbed for orally administered compounds", J. Pharm. Sci., 1985, 74, 588-589) and MAD (Johnson K. et al., "Guidance in the setting of drug particle size specifications to minimize variability in absorption", Pharm. Res. 1996, 13, 1795-1798; Curatolo W., "Physical chemical properties of oral drug candidates in the discovery and exploratory development settings", Pharm. Sci. Tech. Today, 1998, 1, 387-393; and Avdeef A. et al., "HT Solubility and Permeability: MAD-PAMPA Analysis" in: Krämer S. D. et al., "Physicochemical and Biological Profiling in Drug Research", Wiley-VCH: Weinheim, 2006) functions, and the BCS (Amidon G. L. et al., "A theoretical basis for a biopharmaceutic drug classification: the correlation of in vitro drug product dissolution and in vivo bioavailability", Pharm. Res., 1995, 12, 413-420; and "Guidance for Industry, Waiver of In Vivo Bioavailability and Bioequivalence Studies for Immediate Release Solid Oral Dosage Forms Based on a Biopharmaceutics Classification System", FDA, Washington, D.C., USA, August 2000). A union function is proposed herein, for consideration in absorption optimization, called BCG-Mapping. As done in our the permeability-excipient measurements and the solubility-excipient measurements, the mapping scheme shown in FIG. 12c is proposed, using the Biopharmaceutics Classification Gradient Maps, like the one illustrated in FIG. 12c. These are designed to improve the visual aspects of the excipient and all other effects (ABL resistance, membrane retention, aggregation, complexation, pH, and a multitude of other HH-mitigating effects) on the flux function, allowing for precise systematic evaluation. The map can be automatically generated by the ELM software from the company pION associated with the PAMPA and solubility instruments used above. Plotted in FIG. 12c are the summations of the two preceding maps (equation (29) as well as FIG. 12a and FIG. 12b): $\log (P_{e,pH,40}^{X=0}/P_{e,6.2,40}^{X=0}) + \log(S_{pH}^{X}/S_{6.2}^{X=0})$. Such a "gradient" map normalizes flux values to shift patterns with reference to the excipient-free, pH 6.2 baseline. In FIG. 12c, green values represent the base (zero) residuals. Warm colors (yellow to deep orange) represent enhanced flux, and cool colors (deep blue) refer to depressed values. Along the vertical axes are the excipient compositions, rank ordered by decreasing average flux enhancement, considering all the drugs at the three pH values of interest. Along the horizontal axes are the drugs, arranged in the order decreasing benefit due to excipients to the average of the three pH conditions. The top left corner represents the "most benefit" combination of excipients and compounds. The lower right corner represents the "least benefit" combination. With this BCG-Mapping, it is very efficient to recognize and thus prioritize the most promising molecule-excipient combinations, and such mapping schemes can be rapidly acquired for a very large number of molecules, for use in discovery-optimization programs in pharmaceutical companies. The rank ordering based on the flux map is applied to the other two maps, so that direct comparisons are more easily done.

The three most helpful excipients in this first embodiment of the method according to the invention appear to be 0.24% and 1% HP-β-CD, and 3 mM NaTC. Surprisingly, 15 mM NaTC takes the lowest position, due to its strong and general tendency to attenuate permeability (FIG. 12a), not entirely offset by the gains in solubility (FIG. 12b). Other least-effective excipients are 0.24% and 1% PEG400, 0.1M KCl, and 1% PG. These excipients fall below the "none" excipient-free position in FIG. 12c.

From FIG. 12c, it is visually apparent that clotrimazole, with its relatively "warm" colored vertical track in the map in slightly acidic solutions, is ranked the highest overall. Not only is solubility enhanced by the strong excipients, such as 1% HP-β-CD, it is also elevated by moderate and relatively weak excipients, such as 0.2 M KCl. Also, several of the excipients elevate permeability values (FIG. 12a). As BCG-Mapping visually indicates, the flux enhancement of glybenclamide, mefenamic acid, butacaine, and astemizole are weak in several pH conditions, indicating that low solubility (deep blue in FIG. 12b) is partly, but not entirely offset by the enhanced permeability (orange in FIG. 12a). But there are a number of warm islands, e.g., pH 7.4 glybenclamide for a number of excipients, pH 7.4 mefenamic acid with 0.24% PEG400, pH 6.2 mefenamic acid with 0.1 M KCl, etc.

Figure 13:
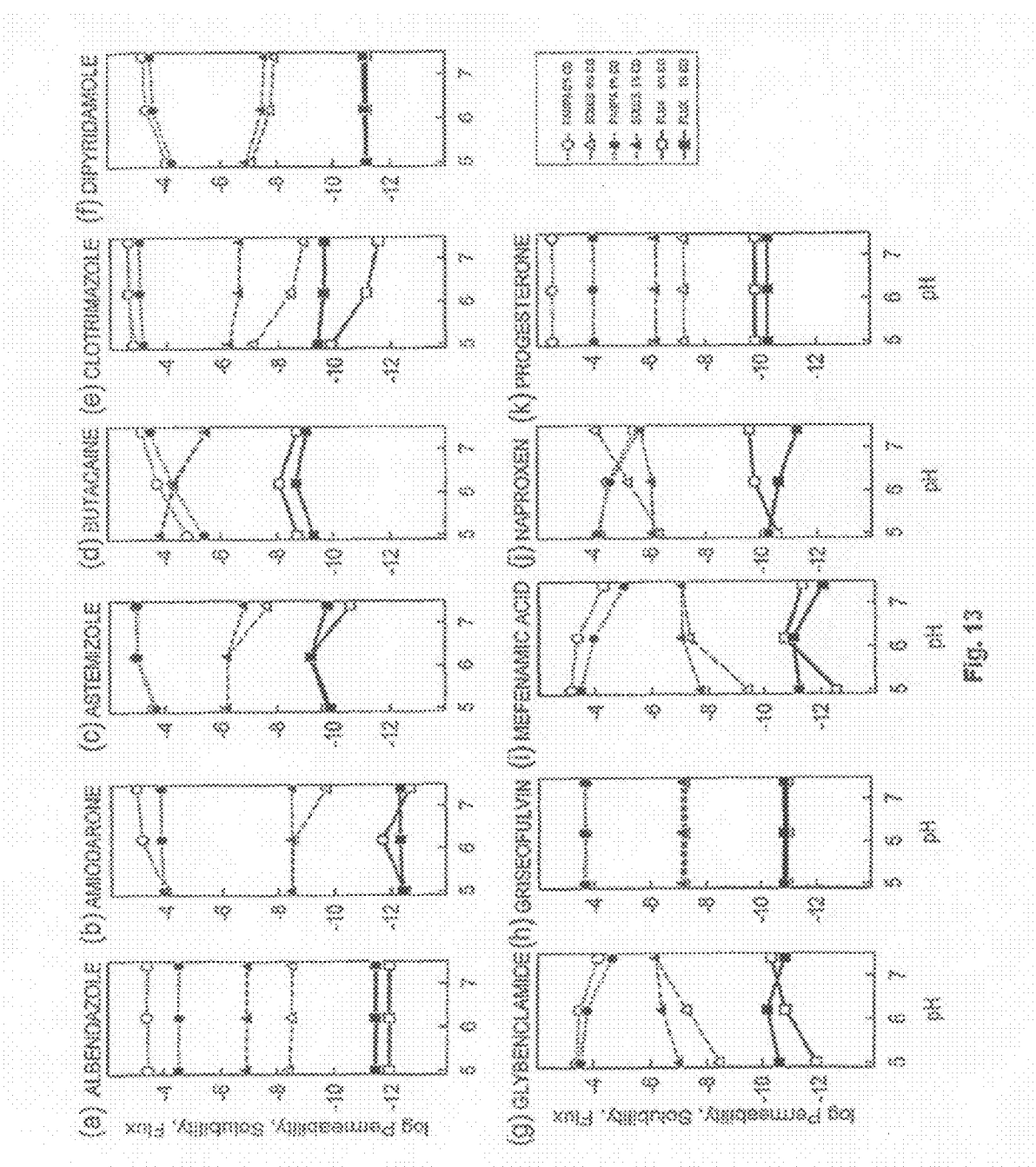
FIG. 13 shows permeability (circles), solubility (triangles), and flux (squares) plots at pH 5.0, 6.2, and 7.4, under excipient-free (unfilled symbols) and in the presence of 1% w/v HP-β-CD (filled symbols) for the method of FIG. 1.

With respect to HP-β-CD effects, cyclodextrin conveyed the best overall benefit to the sparingly-soluble drugs in this set. HP-β-CD data is generated on three additional compounds in the first embodiment of the method according to the invention. FIG. 13 shows the net flux effects due to 1% HP-β-CD for eleven compounds. In general, permeability is decreased by excipients, and solubility is increased by excipients. However, the balance of the two effects is subtle, and could tip the net effect in either direction. FIG. 13 shows various examples of net gain and net loss. Albendazole (FIG. 13a) gains, uniformly at the three pH values of interest, as a result of the excipient, primarily because the gain in solubility was not entirely offset by the loss in permeability. Butacaine (FIG. 13d) loses at all pH values, because the loss in permeability was not recovered, since the 1% HP-β-CD does not improve the solubility in physiological pH to any significant extent. A similar story is evident for naproxen (FIG. 13j). Mefenamic acid is an example of a cross-over effect in pH. In acid solutions, flux is helped by 1% HP-β-CD, but in neutral solutions, there is a net loss due to the presence of the excipient. Dipyridamole (FIG. 13f), shows gains and losses that precisely cancel, and the flux remains unaffected by the excipient. If the oral absorption prediction were based on solubility alone, the inappropriate false-positive classification would have been made. Or the classification would have been false negative, had permeability been solely used in the decision.

The case of amiodarone is difficult to be certain about in the present study. The intrinsic solubility is so low, the "sdiff 3-4" approximation puts a relatively low salt "ceiling" in the solubility curves, the same for all conditions, except excipient-free at pH 7.4 (FIG. 13b). The expected losses in permeability due to the excipient are not well recovered in the net flux, which has a cross-over pattern as a function of pH.

Figure 14:
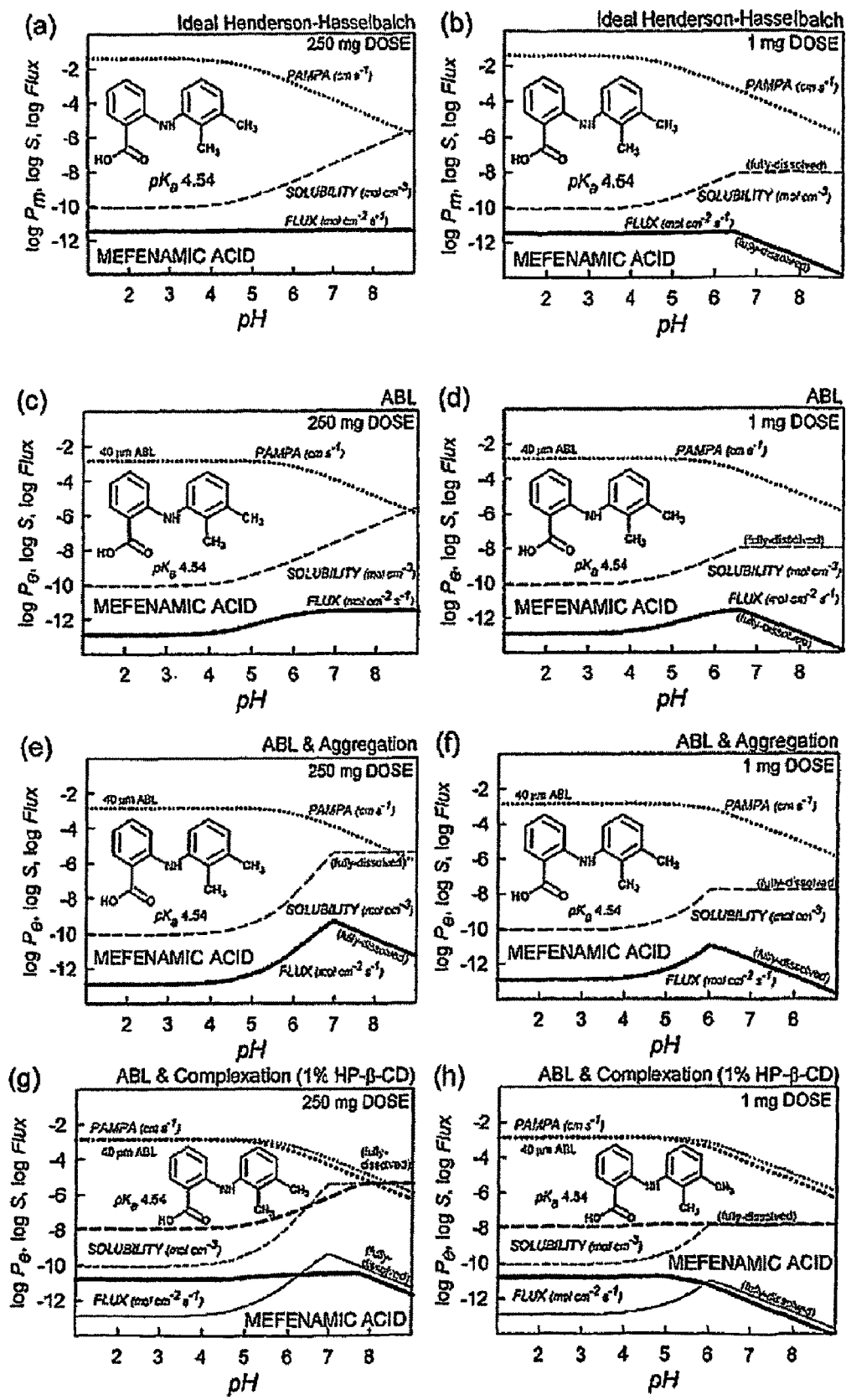
FIG. 14 shows simulated mefenamic acid effective permeability (dotted curve), solubility (dashed curve), and flux (solid line) curves vs. pH.

Regarding the pH partition antithesis, the pH Partition Hypothesis (Shore P. A. et al., "The gastric secretion of drugs: a pH Partition Hypothesis", J. Pcol. Exp. Therap." 1957, 119, 361-369) suggests that mefenamic acid and glybenclamide should be best absorbed in acid pH, because that is the pH where the molecules are least charged. Conversely, clotrimazole, dipyridamole, butacaine, and astemizole should be best absorbed in slightly alkaline solutions, since under such conditions, the weak bases are least charged. However, a quick inspection of FIG. 12c shows that precisely the opposite trends are seen for these molecules. This is especially well evident for clotrimazole, the winner of the excipient game. The sequence of frames in FIG. 14, based on mefenamic acid at and below the clinical dose, will attempt to shed some new light on this surprising and provocative outcome of our study.

FIG. 14a represents the ideal situation, where such "anomalies" as the ABL resistance to permeability, the retention of compound by the membrane, formation of aggregates or complexes, formation of micelle-like structures, precipitation of salts, etc., are assumed to be absent, so that the venerable Henderson-Hasselbalch equation may be applied. Shown in FIG. 14a is the 250 mg clinical dose mefenamic. The pH dependence of permeability mirrors that of solubility, so that each cancels the other in the flux, a product of the two components. So, the simplest view is that absorption should not depend on pH, leading to the trivial but tempting notion that knowledge of the $pK_a$ is not very important in absorption prediction. Note that the pH Hypothesis is violated, since there is no pH dependence in the flux.

FIG. 14b shows the same highly idealized calculation, but in a sub-clinical level of dose of 1 mg. The difference to the preceding case is that above pH 6.5, the compound completely dissolves, and the drug concentration in solution becomes constant, at 1 mg/250 mL (17 µM). Without the precipitate, the flux function takes on a pH dependence (FIG. 14b). In the pH>6.5 region, the classical pH Partition Hypothesis holds.

FIGS. 14c and 14d parallel the preceding two cases, with just one "anomaly": the aqueous boundary layer resistance added to the permeability model. As can be seen in FIGS. 14c,d the top of the permeability curve is depressed by the extent of the resistance imposed by the ABL, whose approximate thickness is 40 µm, modeling that expected in the gastrointestinal tract (Avdeef A., "Absorption and Drug Development—Permeability, Solubility, Charge State, Wiley-Interscience, 2003, pp. 116-246). The added ABL effect causes the flux function to become purely sigmoidal in FIG. 14c. It is remarkable that the pH dependence is opposite of that expected from the Brodie hypothesis. Under sub-clinical dose (FIG. 14d), for pH>6.5, the pH Partition Hypothesis holds, but below that pH, the hypothesis is inverted, and this effect is called the pH Partition Antithesis herein.

FIG. 14e and FIG. 14f bring in an additional "anomaly," that of aggregation, which was observed for mefenamic acid, where anionic dimers and trimers are proposed to explain the solubility-pH curve (see above). The effect of charged aggregates substantially inverts the classical Brodie hypothesis. Because solubility is increased in the region where mefenamic is charged (due to the formation of anionic aggregates), the pH>7 region shows adherence to the pH Partition Hypothesis, even under the clinical dose level of 250 mg. Having a sub-clinical dose (FIG. 14f) just shifts the Brodie pattern to the lower pH 6.

FIG. 14g and FIG. 14h add the effect of the excipient (1% HP-β-CD) to the case of FIG. 14e and FIG. 14f. Apparently, the anti-Brodie effect is nulled, since cyclodextrin appears to bust up the aggregates (FIG. 14e and FIG. 14g). Under the sub-clinical dose, the classical pH Partition Hypothesis fully emerges for the first time in the examples.

Basis for comparing the results of the first embodiment of the method according to the invention to in vivo bioavailability data, the bioavailability of glybenclamide examined in dogs and found that it is significantly increased by cyclodextrin complexation underly as well as the oral bioavailability of albendazole in mice, with and without HP-β-CD found that $C_{max}$ and $AUC_{0-\infty}$ are significantly higher with cyclodextrin than with a suspension of excipient-free drug. Table 3 summarizes parameters from the two pharmacokinetic (PK) studies.

TABLE 3

| COMPOUND | $C_{max}$ (µg/mL) | | | $T_{max}$ (min) | | | AUC (µg/min/mL) | | | Ref. |
|---|---|---|---|---|---|---|---|---|---|---|
| | no excip. | +HP-β-CD | Ratio | no excip. | +HP-β-CD | Ratio | no excip. | +HP-β-CD | Ratio | |
| albendazole (20% w/v) | 0.09 | 0.39 | 4.3 | 45 | 19.8 | 0.4 | 0.0122 | 0.0165 | 1.4 | 33 |
| glybenclamide (gel caps, 200 mg/kg) | 0.0839 | 0.61 | 7.3 | 270 | 150 | 0.6 | | | | 32 |

FIG. 13a and FIG. 13g show the flux function at pH 5-7.4 for albendazole and glybenclamide. These figures show that 1% HP-β-CD does increase the log flux values, but the pH pattern of the effects is different, with glybenclamide showing a substantially more complicated pattern. The flux increases by factors of 3.0, 3.1, and 3.1 for pH 5.0, 6.2, and 7.4, respectively, for albendazole, indicating an average gain by a factor of 3.1. For glybenclamide, the corresponding flux increases by factors of 20.1 at pH 5.0, 4.3 at pH 6.2, but decreases by a factor of 3 at pH 7.4, yielding an average overall gain of 3.1. Table 4 shows that the $C_{max}$ gain ratios for albendazole and glybenclamide are 4.3 and 7.3, respectively. It appears that the flux gradients reported and those found in PK studies are favorably comparable.

A second embodiment of the method according to the invention combines changes in both permeability and solubility to monitor effect of excipients on the absorption potential of compounds without explicitly determining permeability and solubility as separate entities. This makes the second embodiment of the method according to the invention particularly fast. It comprises monitoring the change in concentration of the studied compounds appearing in a receiver chamber of a two-chamber permeation system, the two chambers divided by a lipophilic barrier, while varying the excipient components (type and/or concentration) in a donor chamber. The barrier can constitute an artificial membrane (e.g., a filter impregnated with a lipophilic solution, i.e., the PAMPA model), cultured endothelial cells (e.g., RBE4), or other cultured cell models (e.g., Caco-2, MDCK, etc.). Consideration of the biologically relevant aqueous boundary layer thickness and pH are also taken into account.

Figure 15:
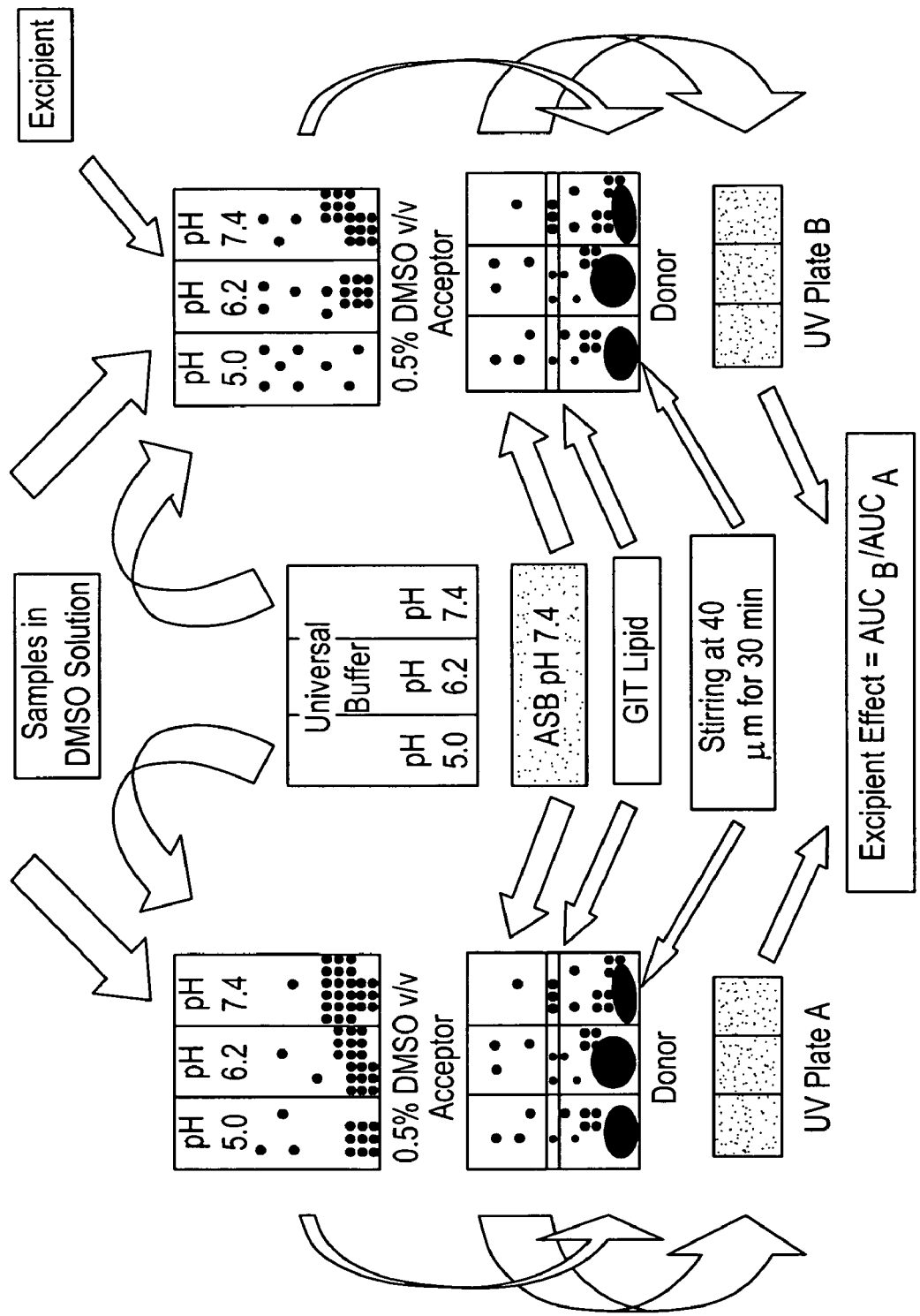
FIG. 15 shows a schematic diagram for experimental setup of a second embodiment of the method according to the invention.

A diagram of the second embodiment of the method according to the invention is shown in FIG. 1. The compounds are presented as DMSO solutions with a concentration of about 10 mM. They are further diluted in a universal aqueous buffer and adjusted to pH 5.0, 6.2, and 7.4 with 0.5 M NaOH. The background amount of DMSO in the aqueous solution is 0.5% v/v. Most of the compounds are insoluble in water, where they form saturated solutions with precipitation present. The calculated concentration of the compounds in the buffer is about 50 μM, but because of precipitation, the actual concentrations in the aqueous media must be lower than that, and are unknown. Saturated (non-filtered) solutions are transferred to the donor compartment of the PAMPA sandwich pre-loaded with magnetic stirrers. The filter of the PAMPA filter plate (the acceptor compartment of the PAMPA sandwich) is covered with GIT-lipid and filled with acceptor sink buffer (ASB). The ASB constitutes a buffered aqueous solution at pH 7.4 with an added surfactant mixture (chemical sink) mimicking the binding properties of proteins in the blood stream (Double-Sink™ PAMPA). Vigorous stirring is employed in the assay, with stirring speed set to produce an aqueous boundary layer (ABL) thickness of about 40 μm, to match the ABL conditions in the GIT. The PAMPA sandwich is assembled and allowed to incubate for 30 minutes in a controlled-environment chamber with a built-in magnetic stirring mechanism. The sandwich is then separated, and the receiver wells are assayed and their UV spectra collected in the UV spectrophotometer (230 to 500 nm). This process is shown schematically on the left of FIG. 15.

The setup is then repeated with the only difference that the donor solution contained excipient in addition to the compound. This is shown schematically on the right hand side of FIG. 15.

It must be noted that stirring plays a key role in the setup of the second embodiment of the method according to the invention. Otherwise any change in permeability of low soluble compounds will be overwhelmed by the resistance of the ABL and thus cannot be detected.

At the end of the assay, the area under the curve (AUC) of the UV spectrum from the receiver compartment of the PAMPA sandwich containing excipient in the donor wells is divided by the corresponding AUC from the PAMPA sandwich with no excipient. The resulting ratio (Excipient Effect) indicates if excipient added to the donor compartment helped improving absorption properties.

Although the method is performed using PAMPA as the permeability system, it can be easily adopted to cellular permeability models (e.g., Caco-2, MDCK, etc.). In fact this assay may be considered as the first approach to in vitro high-throughput PK pre-formulation studies. Indeed, in in vivo PK, by changing the drug formulation and monitoring a concentration versus time profile in the blood stream, a researcher does not directly know the separate influence of solubility or permeability on the final effect, but what matters is the increase or decrease in the concentration of the active ingredient in the blood stream.

Regarding the used drugs and chemicals, the compound used are astemizole, butacaine, clotrimazole, dipyridamole, progesterone, glibenclamide, and mefenemic acid. The Double-Sink™ PAMPA lipid from the company pION (PN 1100669), is stored at −20° C. when not used. The pH of the assayed donor solutions is adjusted with universal buffers from the company pION (PN 100621, 1100151), and the buffer solution at pH 7.4 containing a chemical scavenger to simulate serum proteins is used as the receiver solution. Excipients are added only to the donor wells.

With respect to excipient concentrations a subset of excipients from first embodiment of the method according to the invention described above is identified for demonstration purposes. Quantities of the four excipients are selected to overlap the concentrations expected in the gastrointestinal fluid under clinically relevant conditions. For KCl, concentration of 0.2 M is selected, according to their concentration in FASSIF/FESSIF media. For propylene glycol (PG), 2-Hydroxypropyl-β-cyclodextrin (HP-β-CD), and polyethylene glycol 400 (PEG400), excipient solutions with concentration 1% v/v are chosen to demonstrate the method.

There are three distinct cases evolving as a result of the presented second embodiment of the method according to the invention:

Case 1—excipient effect~1 or log(excipient effect)~0: This outcome means that the receiver concentration is the same regardless of whether excipient X is present in the donor compartment or not. For sparingly soluble compounds this means that either the excipient does not improve solubility or a decrease in the permeability of the compound offsets the increase in solubility.

Case 2—excipient Effect<1 or log(excipient effect)~0: This situation could mean that either the gain in solubility is less than the loss in permeability due to the presence of excipient X or that the compound is fully soluble with or without excipient X and a decrease in permeability is the dominant effect. The result for Butacaine at pH 5.0 demonstrates this situation. It is known from the first embodiment of the method according to the invention, that the solubility of Butacaine in aqueous buffer at pH 5.0 is much greater than 50 μM. Thus, it's not surprising that the absorption behavior for this compound at pH 5.0 is governed by the permeability and that the presence of the excipient in the donor compartment decreases the permeability of Butacaine. The second embodiment of the method of the invention allows detection of this behavior without separate measurements of the solubility and permeability constants, but by simple comparison of the compound concentrations (UV absorbance) in the receiver compartments.

Case 3—excipient effect>1 or log(excipient effect)>0: This result indicates the most promising drug-excipient combination outcome. The greater this ratio, the more effective excipient X is in improving the absorption properties of the studied compound.

Although the second embodiment of method according to the invention is based on one time point, a person skilled in the art can easily adjust it so that the excipient effect is calculated for several time points mimicking an in vivo pharmacokinetics study.

Even though the method according to the invention is described with the exemplary embodiments of above, other alternative embodiments of the method according to the invention are conceivable.

The invention claimed is:

1. A method for assessing effects of excipients, pH and/or combinations thereof on absorption properties of a low solubility compound, comprising the step of assessing a change in a flux function for a plurality of combinations of the low solubility compound and excipients with at least one predefined pH value; wherein the step of assessing the change of flux function comprises the steps of:

(a) providing a calibration donor solution in a first donor chamber separated from a first receiver chamber by a first membrane member, the calibration donor solution comprising the compound and having a predefined pH value; and providing a donor solution in a second donor chamber separated from a second receiver chamber by the membrane member, the donor solution comprising the compound and a first excipient and having the predefined pH value;
(b) providing a receiver solution in the first and second receiver chambers, the receiver solution being free of the compound and the first excipient, and having the predefined pH value;
(c) incubating the solutions for a predefined period of time;
(d) measuring a solubility of the compound in the calibration donor solution and in the donor solution and measuring a permeability of the calibration donor solution and the donor solution by measuring respective amounts of the compound in the donor solution in the first and second donor chambers and in the receiver solutions of the first and second receiver chambers after the incubation;
(e) determining a first ratio between the amount of the compound in the receiver solution of the first receiver chamber and the amount of the compound in the receiver solution of the second receiver chamber;
(f) repeating steps (a) to (e) for a second excipient to determine a second ratio between the measurements of the amounts of the compound in the receiver solution of the first receiver chamber and the measurement of the amount of the compound in the receiver solution of the second receiver chamber using the second excipient; and
(g) assessing changes due to the effects of the first and second excipients by comparing the first and second ratios.

2. The method of claim 1, wherein the step of assessing the change of the flux function further comprises repeating steps (a)-(g) at a plurality of predefined pH values.

3. The method of claim 2, wherein the membrane member is selected from the group consisting of human tissues, animal tissues, plant tissues, cultured-cell models, and artificial membranes.

4. The method of claim 2, wherein the receiver solution comprises at least one additive.

5. The method of claim 2, wherein the additive has at least one of the properties selected from the group of high binding-capacity for the compound, low absorption of ultraviolet light, high water solubility, and low vapor pressure.

6. The method of claim 2, further comprising the step of stirring the calibration donor solution and the donor solution.

7. The method of claim 2, further comprising the steps of: rank ordering the ratios by excipient, compound and pH value; and visualizing the rank ordered ratios.

8. The method of claim 7, wherein the rank ordering of the ratios comprises the steps of: calculating ratio sums for each excipient over all compounds and over all pH values; and rank ordering the ratio sums.

9. The method of claim 7, wherein the rank ordering of the ratios comprises the steps of:
calculating further ratio sums for each compound over all excipients and over all predefined pH values; and
rank ordering the further ratio sums.

10. The method of claim 2, further comprising repeating steps (a)-(g) for a plurality of combinations of a plurality compounds and a plurality of excipients.

11. The method of claim 2, further comprising filtering the solutions and measuring respective amounts of the compound in the filtered solutions.

12. The method of claim 1, wherein the membrane member is selected from the group consisting of human tissues, animal tissues, plant tissues, cultured-cell models, and artificial membranes.

13. The method of claim 1, wherein the receiver solution comprises at least one additive.

14. The method of claim 13, wherein the additive has at least one of the properties selected from the group of high binding-capacity for the compound, low absorption of ultraviolet light, high water solubility, and low vapour pressure.

15. The method of claim 1, further comprising the step of stirring the calibration donor solution and the donor solution.

16. The method of claim 1, further comprising the steps of: rank ordering the ratios by excipient, compound and pH value; and visualizing the rank ordered ratios.

17. The method of claim 16, wherein the rank ordering of the ratios comprises the steps of: calculating ratio sums for each excipient over all compounds and over all pH values; and rank ordering the ratio sums.

18. The method of claim 16, wherein the rank ordering of the ratios comprises the steps of:
calculating further ratio sums for each compound over all excipients and over all predefined pH values; and
rank ordering the further ratio sums.

19. The method of claim 1, further comprising repeating steps (a)-(g) for a plurality of combinations of a plurality compounds and a plurality of excipients.

20. The method of claim 1, further comprising filtering the solutions and measuring respective amounts of the compound in the filtered solutions.

* * * * *